US010111690B2

(12) United States Patent
Anderson et al.

(10) Patent No.: US 10,111,690 B2
(45) Date of Patent: Oct. 30, 2018

(54) ARTHRODESIS IMPLANT AND BUTTRESSING APPARATUS AND METHOD

(75) Inventors: Gregory S. Anderson, Sandy, UT (US); Brock Johnson, Draper, UT (US); Louis Monaco, Salt Lake City, UT (US)

(73) Assignee: Orthopro LLC, Salt Lake City, UT (US)

( * ) Notice: Subject to any disclaimer, the term of this patent is extended or adjusted under 35 U.S.C. 154(b) by 1057 days.

(21) Appl. No.: 13/414,382

(22) Filed: Mar. 7, 2012

(65) Prior Publication Data

US 2013/0066383 A1 Mar. 14, 2013

Related U.S. Application Data

(63) Continuation-in-part of application No. 12/901,552, filed on Oct. 10, 2010, now abandoned.

(51) Int. Cl.
*A61B 17/56* (2006.01)
*A61B 17/86* (2006.01)
(Continued)

(52) U.S. Cl.
CPC ...... *A61B 17/7291* (2013.01); *A61B 17/7233* (2013.01); *A61B 17/1682* (2013.01);
(Continued)

(58) Field of Classification Search
CPC ..... A61B 17/84; A61B 17/844; A61B 17/846; A61B 17/86; A61B 17/8605; A61B 17/8625; A61B 17/863; A61B 17/8635; A61B 17/864; A61B 17/8645; A61B 17/8685; A61B 17/8872; A61B 17/8875; A61B 17/8877; A61B 17/064; A61B 17/0642; A61B 17/0644; A61B 17/0419;
(Continued)

(56) References Cited

U.S. PATENT DOCUMENTS

D277,509 S   2/1985   Lawrence
D284,099 S   6/1986   Laporta
(Continued)

FOREIGN PATENT DOCUMENTS

WO   WO 2010029246 A1 *  3/2010   ............. A61B 17/68

OTHER PUBLICATIONS

Paul, Gerland W., "A New Approach for Correction Hammertoe Deformities." vol. 16, Issue 1. Publication Date: Jan. 1, 2003.

*Primary Examiner* — Kevin T Truong
*Assistant Examiner* — Tracy Kamikawa
(74) *Attorney, Agent, or Firm* — Duane Morris LLP

(57) ABSTRACT

An arthrodesis anchor as a monolithic piece has prongs supporting barbs extending radially therefrom. A neck between the ends may be angled to accommodate final alignment of resected surfaces of joints to be bonded. The neck may receive a tool for buttressing a first inserted end against further penetration into a joint while the second inserted end is inserted into the other adjacent joint. The proximal and intermediate phalangeal joints may be trimmed and pilot drilled, and may be broached with or without a k-wire guide. A first end may be inserted by a tool, typically into the proximal joint, but the order may be reversed. The second end may then be inserted into a pilot in the base of the intermediate joint.

12 Claims, 19 Drawing Sheets

(51) Int. Cl.
*A61B 17/72* (2006.01)
*A61B 17/88* (2006.01)
*A61B 17/84* (2006.01)
*A61B 17/16* (2006.01)

(52) U.S. Cl.
CPC ......... *A61B 17/844* (2013.01); *A61B 17/8872* (2013.01); *A61B 17/8875* (2013.01); *A61B 17/8888* (2013.01)

(58) Field of Classification Search
CPC .... A61B 2017/8655; A61B 2017/0641; A61B 2017/0645; A61B 2017/0646; A61B 2017/0648; F16B 35/00; F16B 35/02; F16B 35/04; F16B 35/041; F16B 35/042; F16B 35/044; F16B 35/045; F16B 35/048; F16B 5/0275; A61F 2/42; A61F 2/4225; A61F 2/4241; A61F 2002/4228–2002/4258
USPC ......... 606/300–331; 411/388, 389, 392, 424, 411/451.1, 452, 455, 456, 451.3
See application file for complete search history.

(56) References Cited

U.S. PATENT DOCUMENTS

| | | |
|---|---|---|
| 5,417,692 A | 5/1995 | Goble |
| 6,319,284 B1 | 11/2001 | Rushdy |
| 6,413,260 B1 | 7/2002 | Berrevoets |
| 6,458,134 B1 | 10/2002 | Songer |
| 6,517,543 B1 | 2/2003 | Berrevoets |
| 7,169,183 B2 | 1/2007 | Liu |
| 2007/0218750 A1 | 9/2007 | Corrao |
| 2007/0233124 A1 | 10/2007 | Corrao |
| 2007/0233125 A1 | 10/2007 | Wahl |
| 2008/0132894 A1* | 6/2008 | Coilard-Lavirotte ........................ A61B 17/1604 606/60 |
| 2008/0319443 A1 | 12/2008 | Focht |
| 2008/0319450 A1 | 12/2008 | Corrao |
| 2010/0057214 A1 | 3/2010 | Graham |
| 2010/0131014 A1* | 5/2010 | Peyrot et al. .................. 606/300 |
| 2010/0286692 A1* | 11/2010 | Greenhalgh et al. ........... 606/63 |
| 2011/0301652 A1* | 12/2011 | Reed et al. .................... 606/319 |
| 2012/0083791 A1* | 4/2012 | Cheney et al. ................. 606/99 |

* cited by examiner

ARTHRODESIS IMPLANT AND BUTTRESSING APPARATUS AND METHOD

RELATED CASES

This patent application is a continuation-in-part of co-pending U.S. patent application Ser. No. 12/901,552, filed on Oct. 10, 2010 and entitled ARTHRODESIS IMPLANT APPARATUS AND METHOD, which is incorporated herein by reference.

BACKGROUND

1. The Field of the Invention

This invention relates to orthopedic surgery and more particularly to methods and apparatus for fixing bone elements in suitable positions for permanent healing.

2. The Background Art

Orthopedic surgeries originated millennia ago. Anthropological excavations have demonstrated orthopedics practices evidenced in healed, sometimes structurally reinforced, bone healing. Modern orthopedic surgery has greatly advanced the art of improving deformities through surgery. Moreover, the importance of maintaining an active life has motivated demonstrably improved methods for promoting the ability to heal.

For example, patients with a variety of recovery needs were customarily committed to bed rest in hospitals in decades past. Modern medicine realizes the emotional and physical toll that such inactivity takes on a patient. Modern surgical techniques acknowledge the importance of maintaining a physically active body as a mechanism to aid in healing processes. Accordingly, it is desirable to have patients continue in their daily movement and activities as soon as possible. To this end, less invasive surgical techniques have been developed.

Likewise, structural implants such as plates, screws, staples, rods, pins and the like have been augmented by new joint systems, and other orthopedic implants to replace or enhance natural orthopedic structures in the body.

Nevertheless, surgical techniques need to be simplified in many instances. Likewise, the speed at which surgical procedures can proceed is limited by both the physical circumstances of the injury or malady being corrected, as well as the equipment used, and any other supporting equipment or devices required by the procedure.

Accordingly, it would be an advance in the art to provide implants, susceptible to faster installation, more secure holding, post-installation tensioning, and the like. Such features would provide to a surgeon the additional benefit of being able to confirm securement. Implants that can originate and enforce angles of relative positioning between adjacent bone elements are also needed.

It would also be an advance if the anchor could support three dimensional stability following surgery in order to hasten healing, permit early use promoting circulation and healing, and otherwise provide securement with less threat of separation, twisting, disorientation, and the like during the important early days of the healing process.

It would be a further advance of the art to provide three dimensional stabilization between two elements being joined in an orthopedic, and particularly a hammertoe remediation, by providing reliable anchoring in the longitudinal direction, as well as orientation in the lateral and transverse directions orthogonal thereto in order that healing begin early and be promoted by stability of the joint in all three dimensions.

BRIEF SUMMARY OF THE INVENTION

In view of the foregoing, in accordance with the invention as embodied and broadly described herein, a method and apparatus are disclosed in one embodiment of the present invention as including apparatus and methods for using implants in arthrodesis surgeries. This application incorporates herein by reference U.S. patent application Ser. No. 12/901,552, filed on Oct. 10, 2010 and entitled ARTHRODESIS IMPLANT APPARATUS AND METHOD.

In one embodiment of an apparatus and method in accordance with the invention an orthopedic anchor, particularly one adapted to arthrodesis, may include two ends of a single, solid member. Typical bone segments may include the proximal and intermediate phalangeal joints of a patient, such as a patient having a hammertoe deformity.

Axially collinear distributions of mutually orthogonal sets of barbs at each end of an anchor may each be oriented along a plane and sized in pitch and depth to promote gripping against not only the structural portion of the marrow or medullar portion of the bone segment into which penetrating, but also to engage the cortical portion of the bone in order to provide a secure longitudinal attachment.

The anchor may be cannulated. The barbs may be non-collinear, with the anchor having a suitable bend built in, such as five, ten, or fifteen degrees between axes on two ends. Accordingly, the length and diameter may be sized to engage the cortical region, and the placement may be selected in order to optimize this engagement.

Opposite ends of the anchor may each be formed as an array of barbed flutes providing a substantially rectangular cross section. As a practical matter, the barbs may actually be considered circular, but typically having flats formed in diametrically opposed sides. Thus, the fluted, arcuate portions of the barbs may extend laterally in one dimension, but be absent at ninety degrees therefrom.

Likewise, a slot may be formed in each end of the anchor to extend between the two flat aspects of the barbed ends. In this way, a tool may be fitted against the flats, having a web connecting between the flats, and extending through the slot formed between the barbs. Various other webs may be formed in tool or barbs in order to stabilize the two prongs or legs of a barbed end with respect to one another, minimize the unsupported length thereof, and the like.

A surgeon may maintain surface alignment and contact between the resected contact faces of the bone elements being joined. Likewise, those faces may be canted slightly with respect to one another, and so maintained by an angle in the longitudinal axis of the anchor, in order to maintain the desired orientation.

In certain embodiments of an apparatus and method in accordance with the invention, an anchor may be pre-angled to match a tool provided with a web exactly matched to fit any "misalignment" of that angle of the barb with respect to the longitudinal axis of the end first inserted during surgery.

The web of the tool angles to accommodate the longitudinal axis of a first set of barbs, thus providing axial alignment between the handle of the tool and the longitudinal axis of the set of barbs at the opposite end.

In this way, the web of the tool provides a "dogleg" effect countering the angle between the prongs at opposite ends of the anchor 10 presenting the barbs held in the tool, so the longitudinal axis of the inserted barbs are axially aligned along a longitudinal axis of the handle, even collinear therewith. Meanwhile, the handle end of the tool aligns at all times with the barbs being first inserted.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
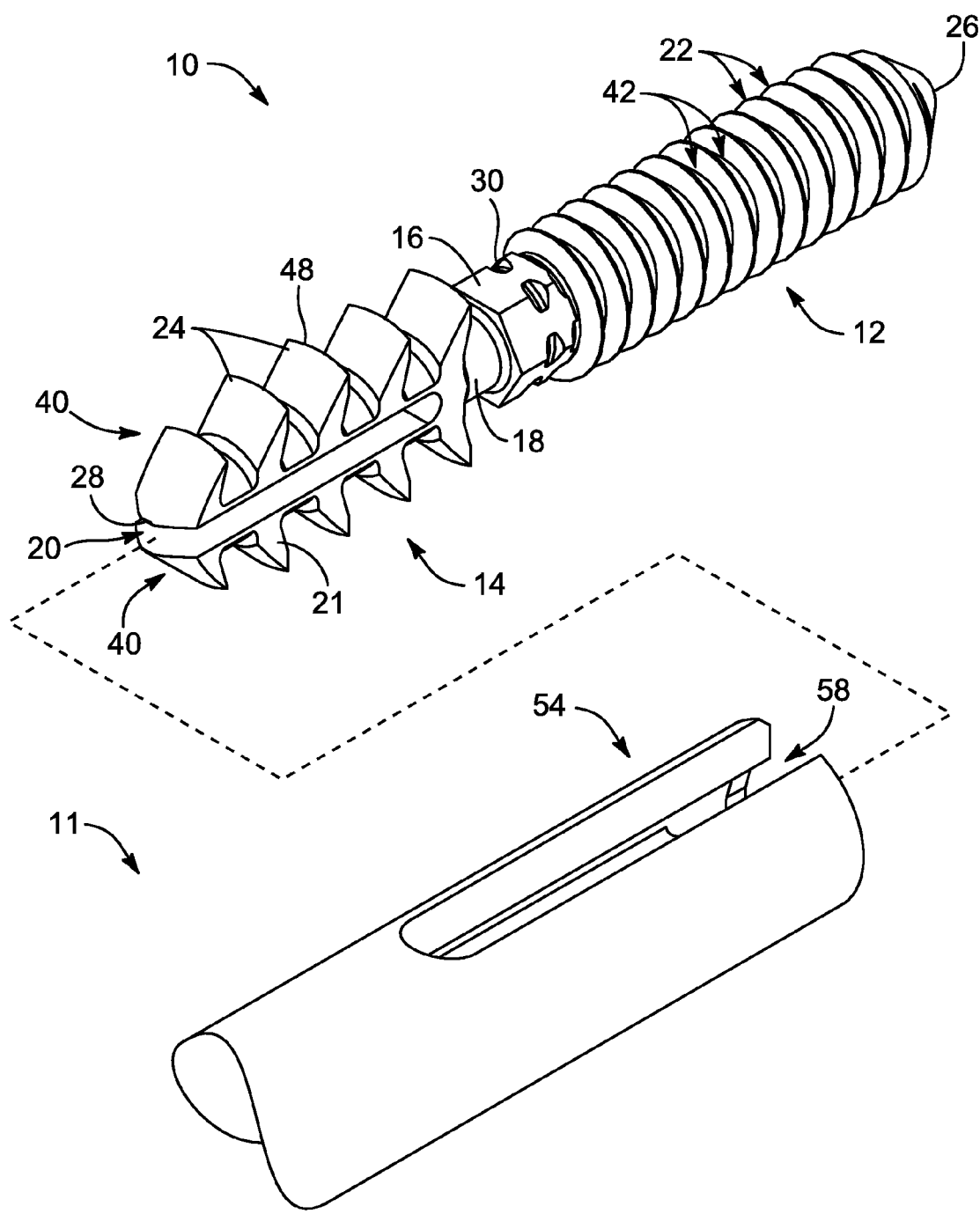
FIG. 1 is a perspective view of one embodiment of an apparatus in accordance with the invention including both an anchor and a tool for manipulating the anchor during initial stages of the installation process.
Figure 2:
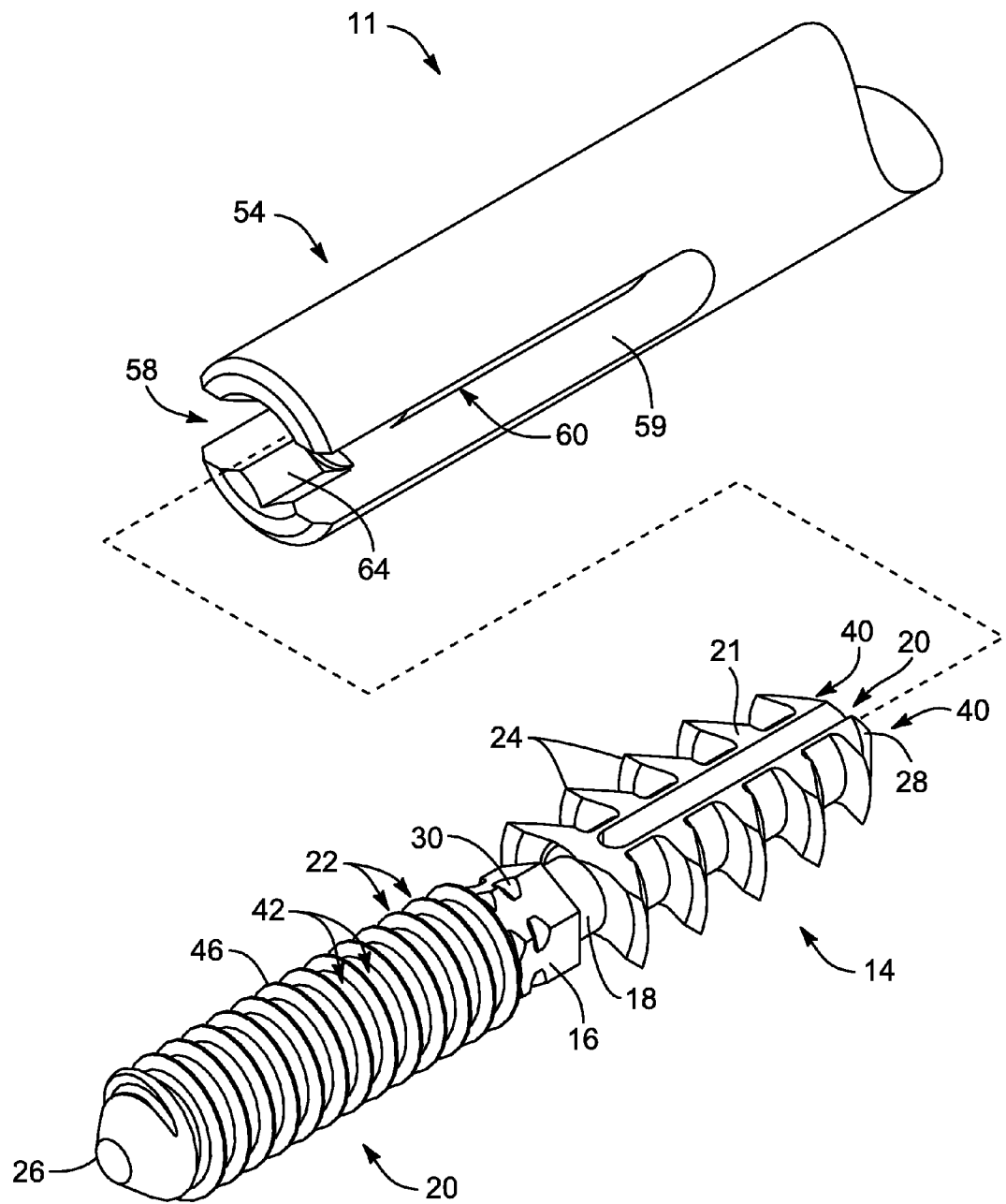
FIG. 2 is a perspective view of the anchor and tool of FIG. 1, viewed from the opposite end thereof.
Figure 3:
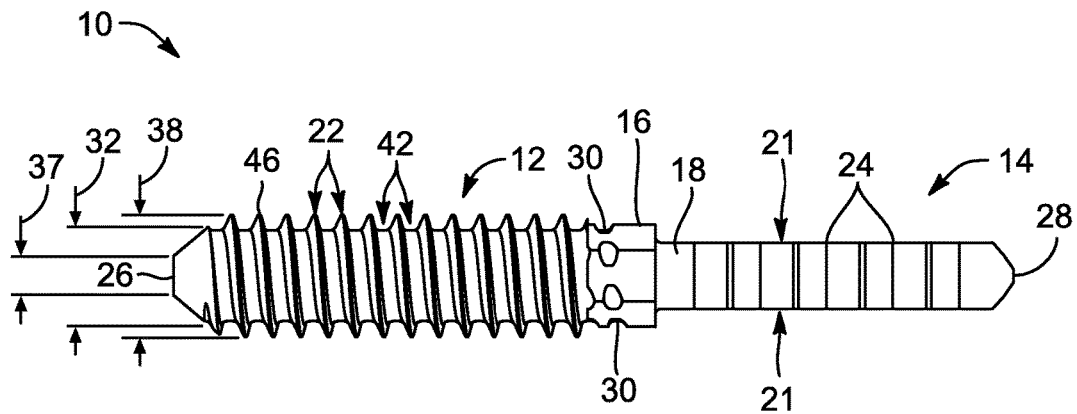
FIG. 3 is a top plan view of the anchor of FIG. 1.
Figure 4:
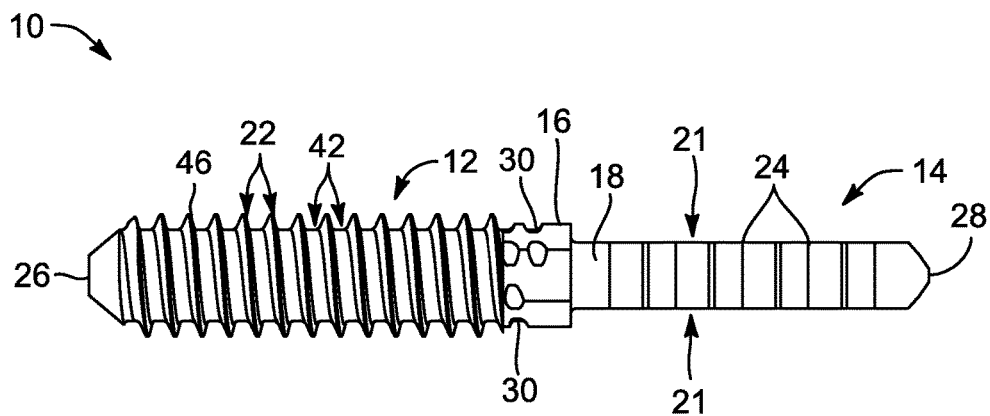
FIG. 4 is a bottom plan view thereof.
Figure 5:
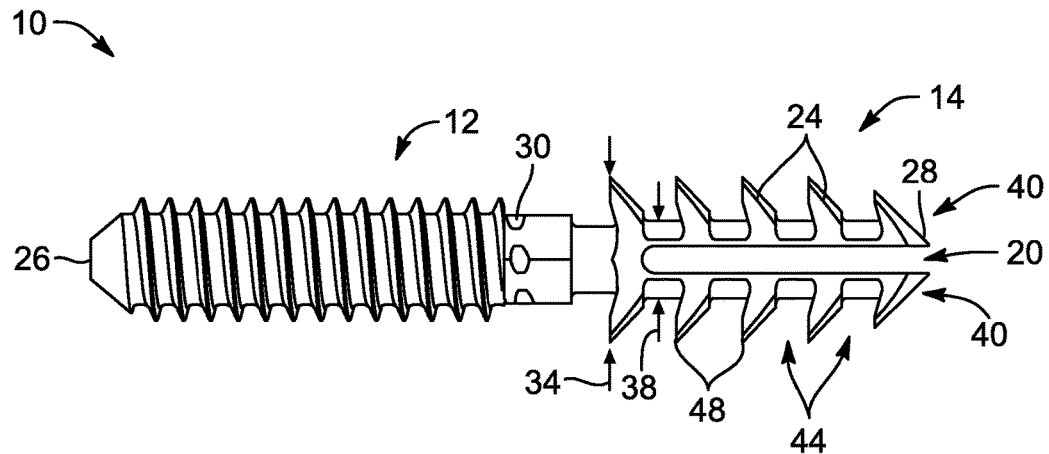
FIG. 5 is a left side elevation view thereof.
Figure 6:
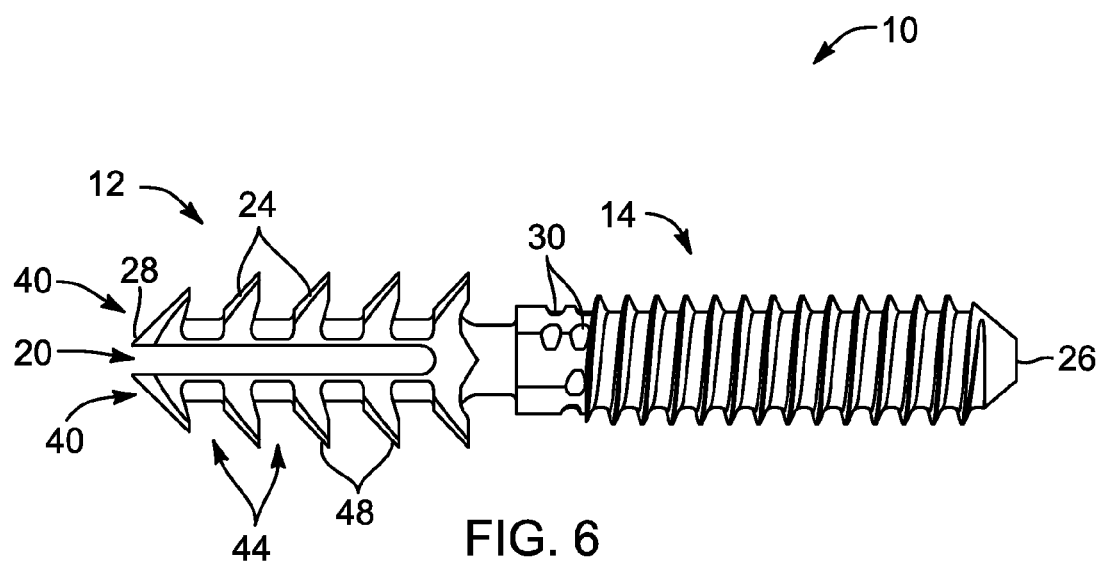
FIG. 6 is a right side elevation view thereof.
Figure 7:
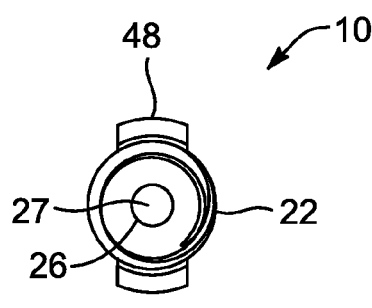
FIG. 7 is an end elevation view from the screw point end.
Figure 8:
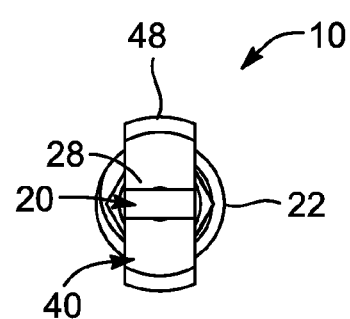
FIG. 8 is an end elevation view thereof showing the pronged or barbed end that is engaged by the tool.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, while referring generally to FIGS. 1-31, a system 10 or apparatus 10 in accordance with the invention may include an anchor 10 that may be manipulated and applied using a tool 11. The anchor 10 includes a screw portion 12 or a screw 12 formed in a unit with a barb portion 14 or barb 14. In the illustrated embodiment, the screw 12 and barb 14 portions are formed together of a single, homogeneous material simultaneously formed in any suitable manner.

In certain embodiments, the apparatus 10 may be formed to be of a biodegradable material. Nevertheless, in other embodiments, durable materials that are not rejected by the body may be used. For example, stainless steel, titanium, and the like have been found suitable for applications useful for anchors 10 in accordance with the invention.

The anchor 10 may also be formed to include a shank 16 or a shank portion 16. In certain embodiments, it has been found that the shank 16 is best located immediately adjacent the screw portion 12. In application, the screw 12 may be threaded into a portion of bone, typically the medullar portion. Accordingly, the shank 16 may follow the screw 12 into the medullar portion of a bone joint segment with the shank 16 sunk into the bone until the end of the shank 16 farthest from the screw 12 is flush with the surface thereof.

In addition to the shank 16, the anchor 10 may include a shaft 18 or neck 18 between the first inserted portion 12, which may be a screw portion 12 and the later inserted portion 14 or barb portion 14.

In some embodiments, the shaft 18 may be pre-angled in order to provide a known and desired angular difference between the orientation of the portion 12 and the portion 14 of the anchor 10 once installed. In this way, a pre-determined angle may exist in the shaft 18.

In the illustrated embodiment, an anchor 10 may include a slot 20. The effect of the slot 20 is to form a cantilevered, pronged arrangement. Also, the slot 20 may serve to engage the tool 11 in order to drive the anchor 10 into a bone joint for a surgery. The slot 20 may also provide a region in which tissue will reform and fill up, further stabilizing the anchor 10 once in place. Typically, an anchor 10 is not removed. Rather, the anchor 10 stabilizes a surgery, and remains in place after healing is complete.

A screw portion 12 may include threads 22 at a selected pitch, depth, advance angle, and the like, which threads 22 may be buttressed such that they tend to be supported more against force or deflection in one direction than another.

By the same token, the barb portion 14 may include a plurality of barbs 24, the barbs may act on cantilevered arms in order to pass through a pilot hole, and then work out into the medullar region of the bone, ultimately engaging the cortical portion thereof. Likewise, barbs 24 are best engaged into cortical material of the bone, the outer shell like portion that is more dense, stronger, and much harder than the medullar or central region of the marrow.

In order to facilitate an insertion, the screw end 12 may have a point 26. Also, the screw 12 may be cannulated or hollow. Thus it may not form a sharp point 26.

Likewise, the barb portion 14 may include a point 28 associated with the first of the barbs 24. Like the opposite end 12 of the anchor 10, the point 28 at the barb portion 14 of the anchor 10 may be sized to fit or otherwise engage a pilot hole. A pilot hole could be simply drilled at a single diameter or broached larger, and the barb point 28 may engage that resulting hole.

Referring to FIGS. 1-8, and more generally to FIGS. 1-31, an anchor 10 in accordance with the invention may be provided with cavities 30 configured to receive tissue growth therethrough or may simply have a single cavity 30 cannulated along the entire length.

A screw 12 may have an outer diameter 32 defining the outermost edge of the flutes or threads 22 thereof. Meanwhile, the outermost diameter 34 of the barbed portion 14 will typically follow an arcuate path, although not usually for a full circle. That is, the barbs 24 are formed to present a flat aspect 21 that assists in stabilizing the barbs in place, reduces the requirement in the size of the pilot hole required, and also provides for cantilevering of the barbs 24 in order that they may ultimately extend to their maximum outside diameter 34 to engage the cortical portion of the bone.

Meanwhile, the threads 22 have an inner diameter 36 that defines the valley, trough, or the relief that exists at a lesser diameter than the outer diameter 32 of each of the flutes 22 or threads 22. Moreover, the screw 12 may also have an innermost diameter 37 that represents a cavity or cannulation 30 formed as a tubular vacancy along the center of the anchor 10.

As with the screw portion 12, the barbed portion 14 has an outer diameter 24 as well as an inner or minor diameter 38 with the cannulation 30 forming an inside diameter 37. The inner diameter 38 provides for additional material, provides for a smooth and arcuate surface, and provides additional stiffness for the barb portion 14. Effectively, the barb portion 14 is divided into two prongs 40. Each of the prongs 40 contains an array of barbs 24, the first one representing the point 28.

Thereafter, the barbs 24 may increase in diameter or simply have a larger outer diameter 34 than the first barb. Each of the barbs 24 has an outer diameter 34 at which it engages the bone, and an inner diameter 38 that represents effectively the outermost fiber of a beam that cantilevers or carries the barb 24. That beam 40 is one of the prongs 40 arrayed with barbs 24 therealong.

Thus, each of the threads has a gap 42 or pitch 42 between threads. Similarly, each of the barbs 24 has a pitch 44 or maximum gap 44 as a center-to-center or edge-to-edge distance 44.

In contrast, the gaps 44 may initially be less filled with bone material inasmuch as the barbs 24 must pass therethrough. However, the cantilevered effect of the prongs 40 permits the barbs 24 to move toward one another, forced by the pressure of the surrounding bone. Nevertheless, upon the slightest provocation to retreat, or upon coming to rest, the prongs 40 are urged apart by their inherent elasticity, causing each of the barbs 24 to move out toward its edge 48. The edges 46 of the screws 12 or the edges 46 of the threads 22 will cut into and anchor against the bone material, and particularly against cortical material. Likewise, the edges 48 of the barbs 24 will tend to advance outward as they come to rest, cutting through the medullar material and engaging the cortical material of the bone.

Figure 9A:
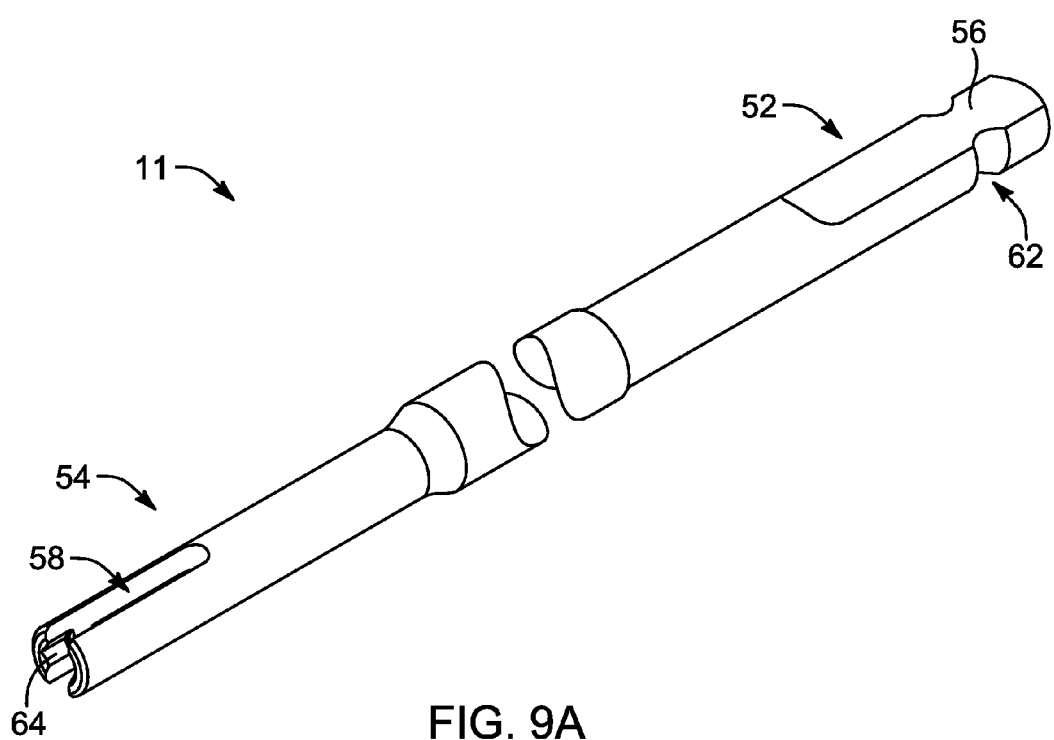
FIG. 9A is a perspective view of one embodiment of the tool of FIG. 1, having the center portion shortened as indicated in order to provide detail of the handle and anchor ends thereof.
Figure 9B:
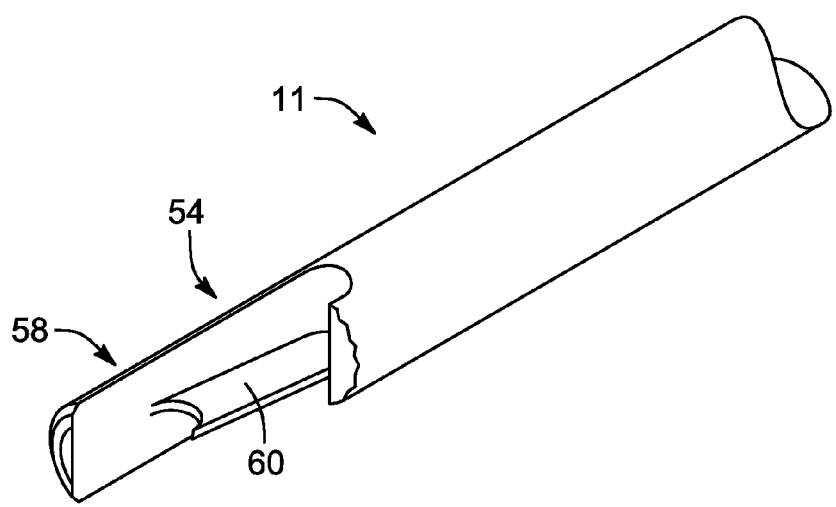
FIG. 9B is a cutaway perspective view of an alternative embodiment of the insertion tool or instrument.

Referring to FIGS. 9A and 9B, while continuing to refer generally to FIGS. 1-31, a tool 11 in accordance with the invention may be formed with a receiving portion 54 to fit over part of the anchor 10. Accordingly, opposite the receiving portion 54 of the tool 11, a handle portion 52 may be adapted to be gripped by a hand of a surgeon. For example, the handle portion 52 may include a flat 56 as well as relief 62 for gripping.

Any time relief is provided, such as by notching, knurling, or the like, the handle portion 52 may be more readily gripped because flesh from the hand of a user expresses into the slot or relief area providing better than a frictional grip thereon. Accordingly, the tool 11 may include a flat 56, a relief slot 62, knurling, or the like in order to provide better grip of the tool 11 for a surgeon. Accordingly, a surgeon user may thereby handle with greater security the tool 11 in order to drive the anchor 10 into a bone joint 70 where the anchor 10 will serve to stabilize the conjoining of two joints 70, 74 during healing.

Likewise, the anchor portion 54 or the receiving portion 54 of the tool 11 may include a slot 58 to receive the back or later inserted barb portion 14 of the anchor 10. Specifically, the prongs 40 that form the main beams 40 of the rear or later inserted barb portion 14 may fit within the slot 58, sized to receive it.

Referring to FIGS. 9A-9B, in certain embodiments, a web 60 may extend between opposite faces of the slot 58 in order to engage the slot 20 in the anchor 10. Thus, the barb portion 14 is engaged on the flats 21 by the opposing faces that form the slot 58. Meanwhile, the slot 20, and the inner faces of the secondary, back, or later inserted barb portion 14 that form the slot 20, are engaged by the web 60. The web 60 may be angled so the first-inserted portion 12 is aligned, or even coaxial or collinear, therewith.

In certain embodiments, a relief 64 may be formed to receive a hexagonal or other shape of the shank 16. Thus, the anchor 10 may be engaged by the tool 11 by the slot 58 engaging the flats 21 of the barb portion 14, the web 60 engaging the faces of the slot 20 in the barb portion 14, and the relief section 64 fitted to the shank 16 for engaging the shank 16 therein.

In an apparatus and method in accordance with the invention, a tool 11 or instrument 11 may be formed to serve as an anchor 10 that has a pre-determined offset angle between the longitudinal axes of the barb portions 14a, 14b of the anchor 10. In one embodiment of an apparatus and method in accordance with the invention, the tool 11 may be formed to receive an anchor 10 having a pre-determined angle of bending of the shaft 18 or neck 18 thereof.

Thus, the web 60 is oriented at the same angle as that in the anchor portion 54 of the tool 11. The angle provides the direction required to accommodate a second inserted barb portion 14b of an anchor 10. Placing that end 14b of an anchor 10 into the anchor portion 54, and the slot 58 particularly, of the tool 11, the first inserted portion 14a is aligned parallel with the handle 52. The longitudinal axis thereof is in alignment, and preferably collinear with, the longitudinal axis of the handle portion 52 of the tool 11.

Upon completing the process of inserting a first inserted portion 14a of the anchor 10, a surgeon may draw the handle portion 52 away from the anchor 10, and thus remove the slot 58 and web 60 from engagement with the second inserted barb portion 14b of the anchor 10.

Line-of-sight alignment may be enhanced by the handle progressing continuously in the longitudinal direction. Thus, with the first inserted portion 14a extending therefrom, natural line of sight and natural eye-to-hand coordination may aid orientation of the tool 11.

Extraction of the tool 11 after installation of the anchor is along the longitudinal axis of the second inserted barb portion 14b. For example, the slot 58 of the tool disengages from the flats 21 of the barbs 24, while the slot 20 of the barb portion 14b disengages from the web 60 of the tool 11.

The tool 11 is configured to receive one end 14a, 14b of the anchor 10, fitted in the slot 58, with the slot 20 of the anchor fitted over the web 60. The web 60 is angled to match the pre-set angle in the neck 18 of the anchor 10, such that the remaining end 14b, 14a is oriented collinearly with the tool 11 for insertion.

That pre-set angle between the two barb portions 14a, 14b is best formed in the neck 18 of anchor 10 at manufacture and not achieved by bending the neck 18 at anytime thereafter. This is usually so, regardless of which types of ends 12, 14 are used. It is even more important if the anchor 10 is cannulated. Typical pre-set angles of zero, five, ten and fifteen degrees may be used to accommodate the relative angle needed between two joints 70, 74. Most commonly, ten and 15 degree angles are used if any angle at all. Accordingly, the apparatus and method of each embodiment may be employed in a manner similar to that for the other embodiments, with variations only as required.

Figure 9C:
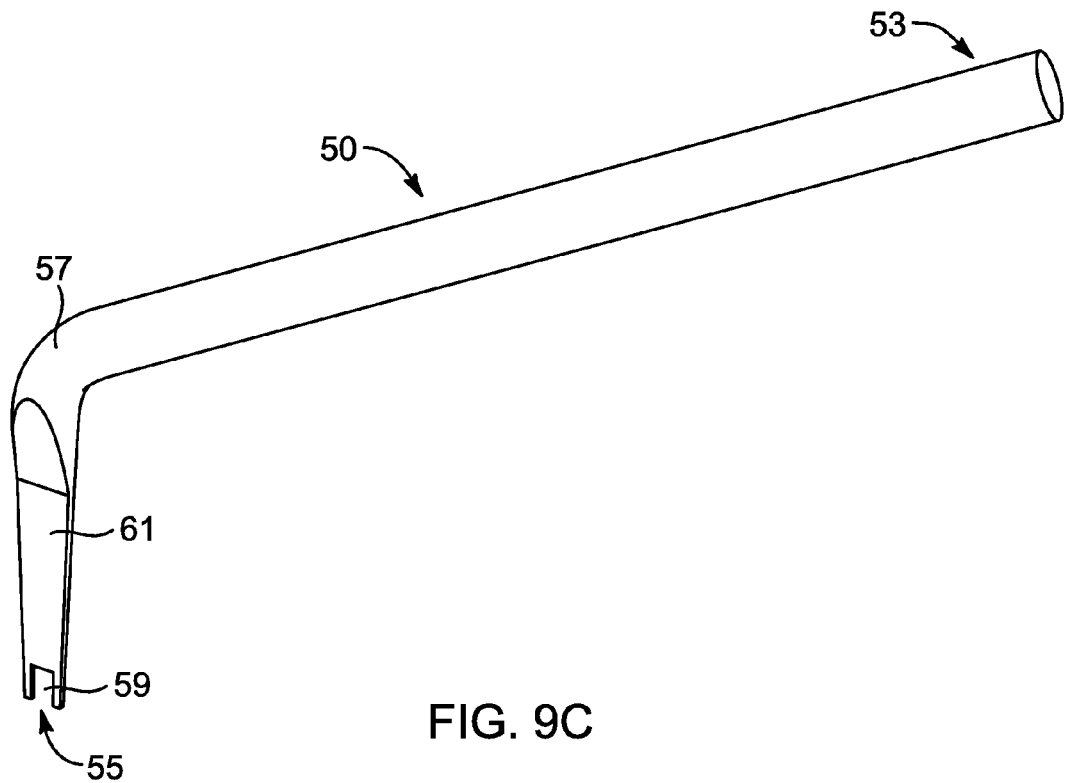
FIG. 9C is a perspective view of a buttress tool used for limiting motion of an anchor during insertion into a second joint.

Referring to FIG. 9C, a buttress tool 50 may be formed with a handle 53 or handle portion 53 extending at sufficient length to be easily grasped by a hand of a surgeon. A corner 57 or angle 57 between the handle 53 and the main face 51 provides visibility of the face 61 while holding the handle 53 at a convenient angle in use.

At the distal end 55 or extremity 55 of the face 61 away from the handle 53, a slot 59 is formed in the face 61. The size and shape of the slot 59 are formed to engage a receiving portion of the neck 18 or shaft 18 on the anchor 10.

The anchor receiving portion 55 or the operational end 55 of the tool 50 is inserted into the space between two joints during surgery. Accordingly, the slot 59 engages the neck 18, at a position effective to hold the anchor 10 from proceeding any further into a first joint.

For example, when a second joint is forced onto the opposite end 14a, 14b of the anchor 10, the face 61 against the first joint precludes any motion of the anchor 10 further into that first joint. Accordingly, the second joint may then be engaged onto the second end 14b, 14a of the anchor 10 until the second joint comes flush against the face 61. At that point, the mere thickness of the anchor-receiving end 55 of the tool 50 remains between the joints. That end 55 is comparatively thin, and may actually be less than the pitch between the barbs 24.

Thus removing the buttress tool 50 makes possible the movement of either end 14a, 14b of the anchor 10 into its respective joint. However, any favoring of one over the other is not problematic, because the overall distance (e.g., thickness of the end 55) remaining is insignificant.

Figure 9D:
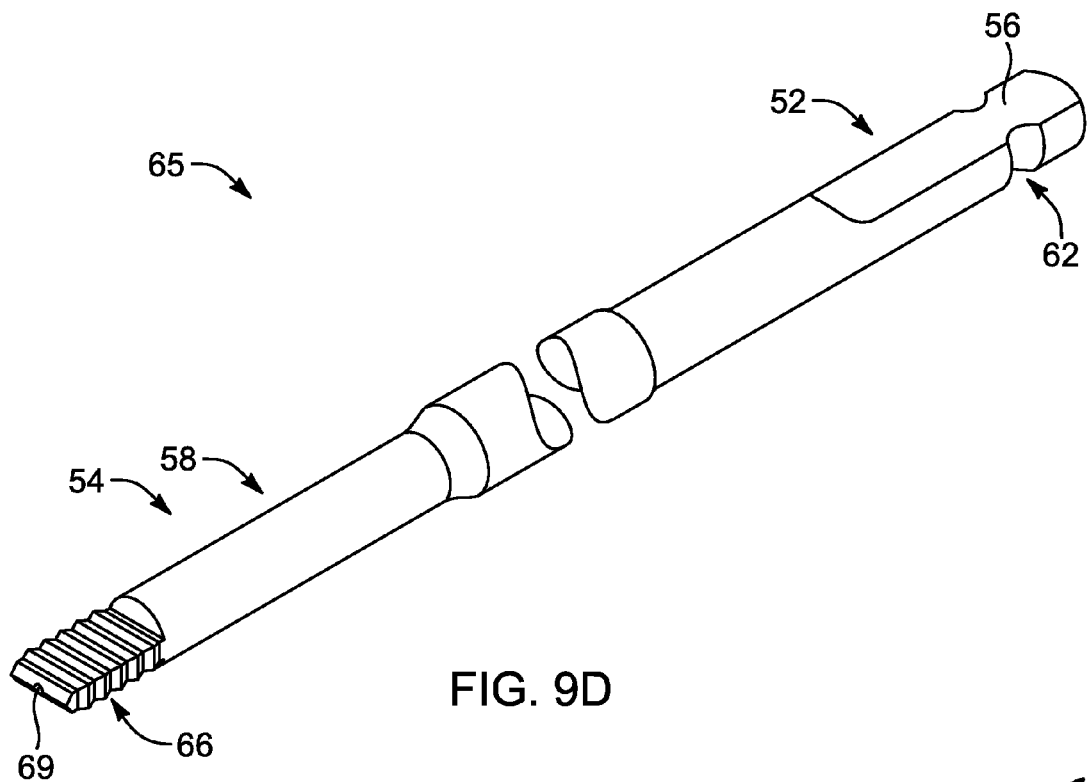
FIG. 9D is a perspective view of one embodiment of a broaching tool suitable for enlarging a pilot hole in a joint for rendering a joint suitable to receive an apparatus in accordance with the invention.
Figure 9E:
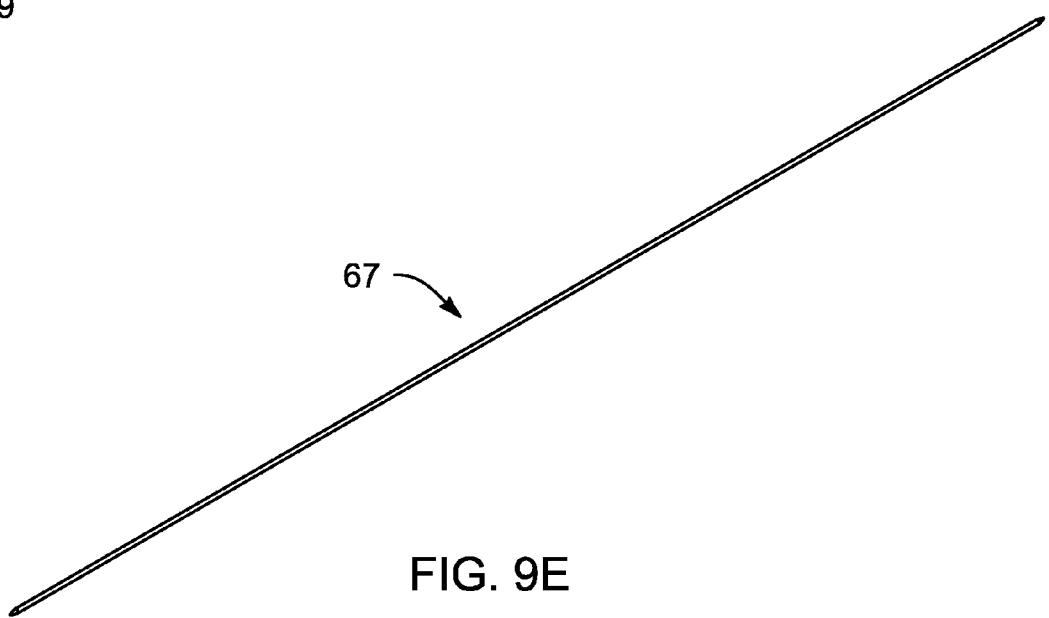
FIG. 9E is a perspective view of a K-wire rod having both ends surgically sharp for insertion into the medullar portion of a joint for effecting a surgical method in accordance with the invention.
Figure 9F:
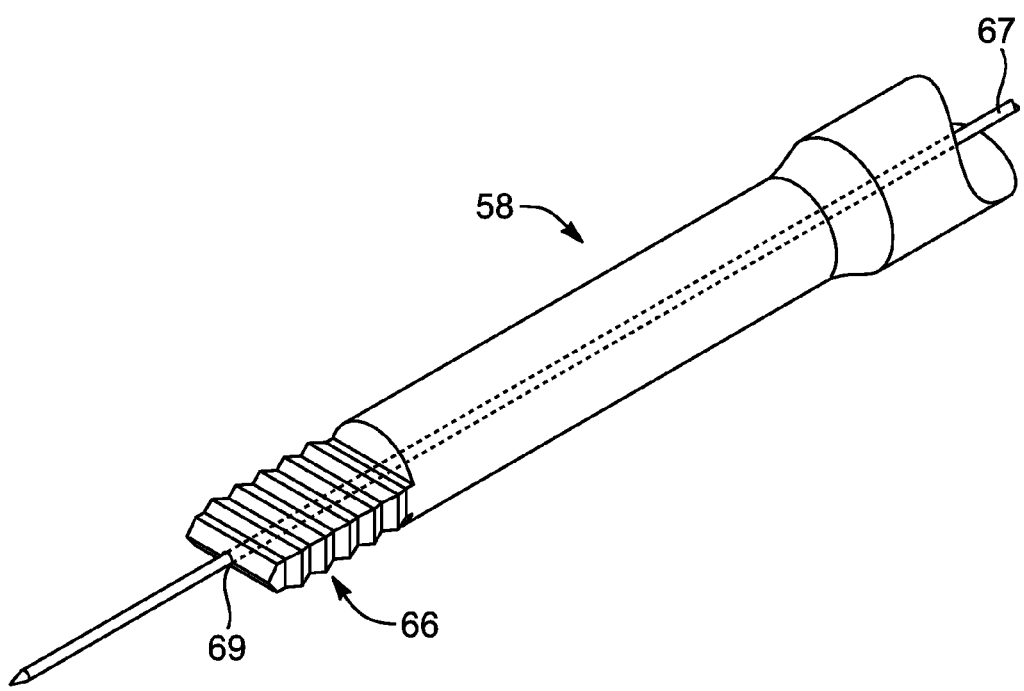
FIG. 9F is a perspective view of one embodiment of the broach of FIG. 9D traveling along a K-wire of FIG. 9E in one embodiment of a method in accordance with the invention.
Figure 10:
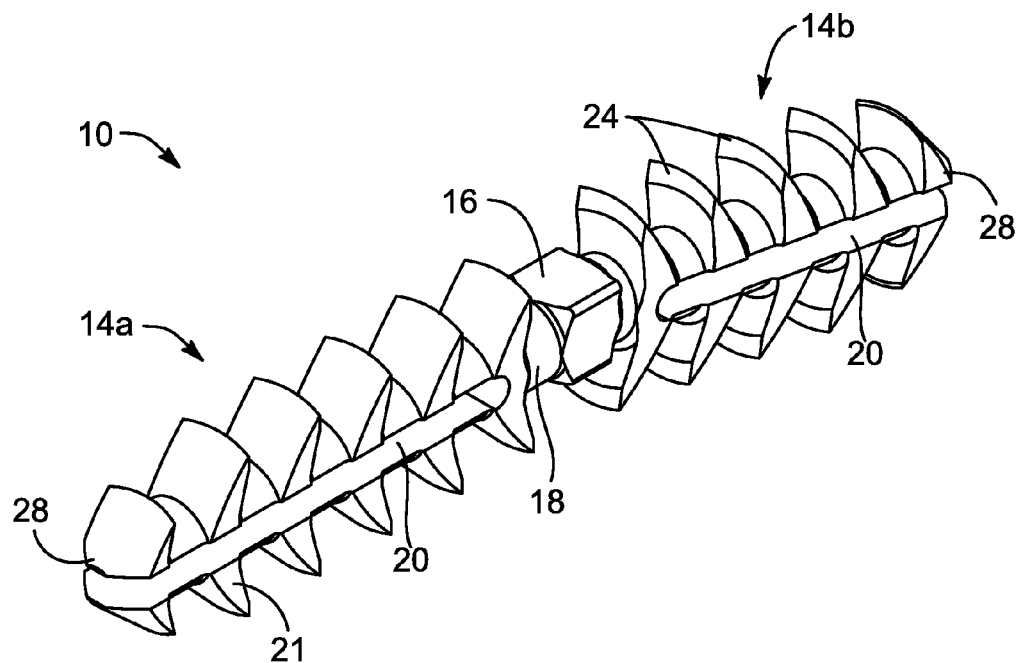
FIG. 10 is a perspective view of an alternative embodiment of an anchor in accordance with the invention relying on two barbed ends, and having a pre-formed bend angle between the longitudinal axes thereof.
Figure 11:
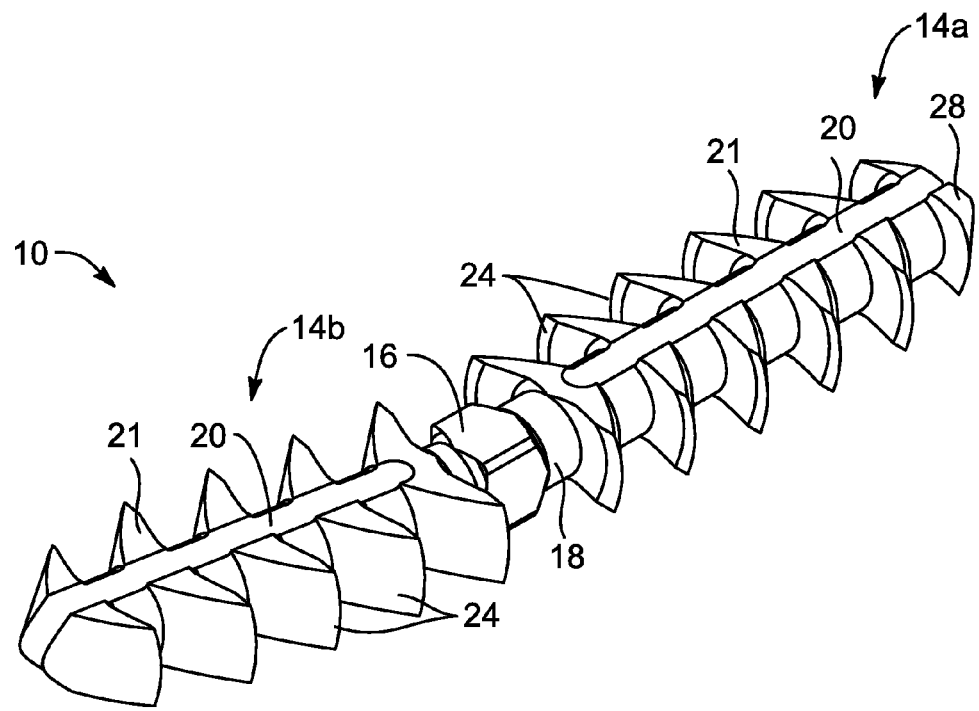
FIG. 11 is a perspective view thereof from the opposite end, and rotated at right angles about a longitudinal axis.
Figure 12:
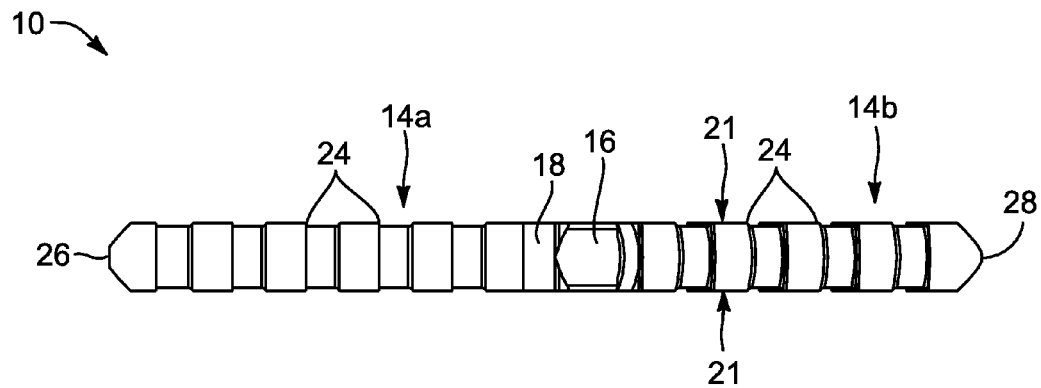
FIG. 12 is a top plan view of the embodiment of FIG. 35.
Figure 13:
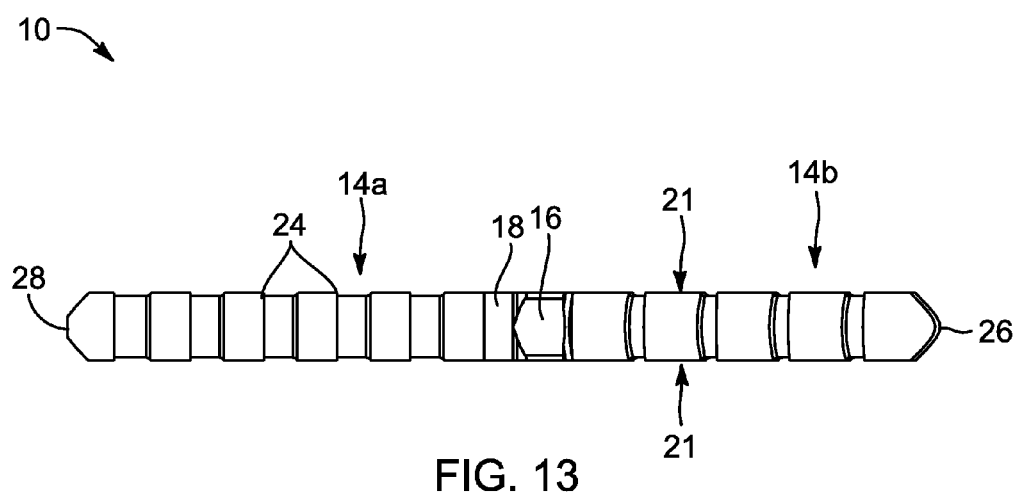
FIG. 13 is a bottom plan view thereof.
Figure 14:
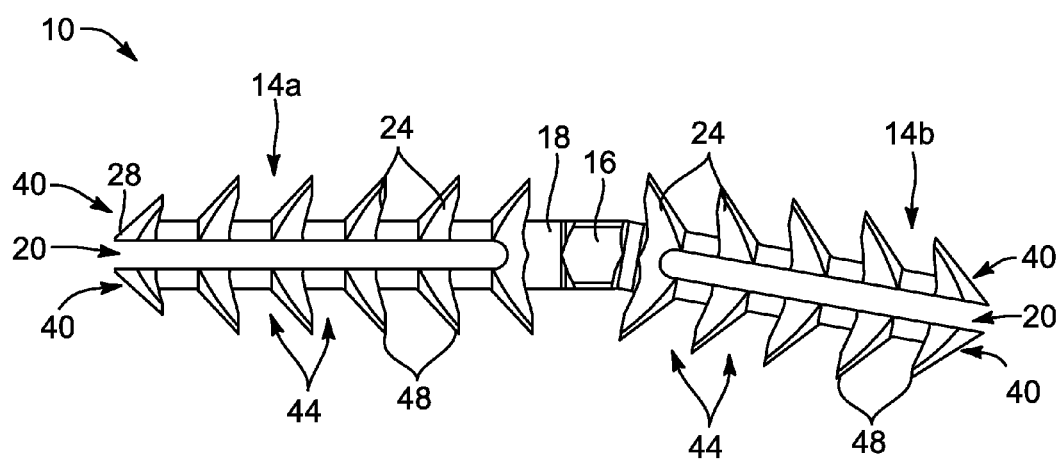
FIG. 14 is a left side elevation view thereof.
Figure 15:
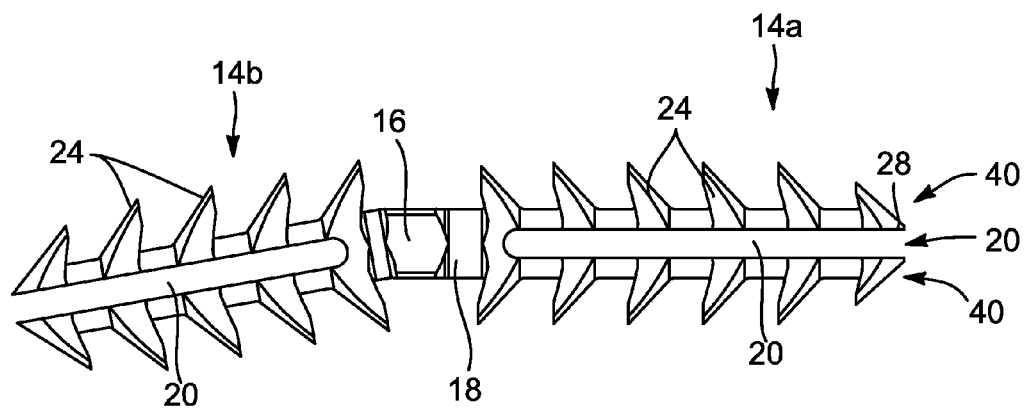
FIG. 15 is a right side elevation view thereof.
Figure 16:
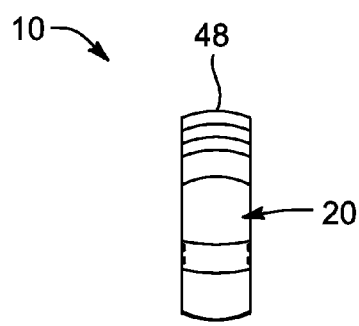
FIG. 16 is an end elevation view thereof from the back end having fewer barbs.
Figure 17:
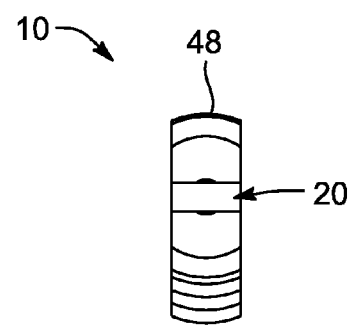
FIG. 17 is an end elevation view from the opposite end thereof.

Referring to FIGS. 9D-9F, a broach 65 or a broaching tool 65 may include a handle portion 52 and a forward end 54 holding the actual broaching region 66 or cutters 66 for broaching an aperture in a joint. Thus one may properly speak of the broach 65 or the broach 66.

In the illustrated embodiment, the broach 66 may be of any suitable size, and multiple tools 65 may be used. One may rely on a sequence of broaches 66 of progressively larger sizes. Thus, initially, a surgeon may begin with a pilot or pilot hole 76, formed with an awl or a drill. Subsequently, various sizes of broaches 66 may be inserted and drawn axially back and forth repeatedly. Each further opens the aperture 78 initially formed as a pilot 76. Ultimately, the broached opening 78 or canal 78 is shaped to be the size and shape of the largest broach 66 used, and of a suitable depth and dimension for an anchor 10 selected.

Referring to FIG. 9E, a K-wire rod may be used, an includes double trocars (i.e., pointed ends) as well as the main shaft 67 or rod 67 thereof. In some embodiments, the K-wire 67 may be used exclusively during surgery as a penetrating guide. In other embodiments, the K-wire 67 may be left in place after completing an arthrodesis reduction. In such case, it may be withdrawn after the degree of healing has reached a predetermined stage.

Referring to FIG. 9F, the broaching tool 58 may include a cannula 69 sized to freely receive the K-wire 67. In operation, the K-wire 67 may penetrate into a pilot 76, thus acting as a guide 67 along which the cannula 69 will slide. Accordingly, the broach 66 or broach cutters 66 may thus be guided.

This ensures that the broached opening 78 formed thereby is not misaligned or oversized. An oversized opening 78 will not be suitable to receive and engage the barbs 24 of an anchor 10 if oversized too far. The broaching tool 58 may slide forward and backward along the K-wire 67, thus alternatively penetrating into the medullar portion of the joint 70, 74 and then retreating with the cutters 66 drawing out the cuttings from the broached opening 78.

Referring to FIGS. 10-17, in one embodiment of an apparatus 10 in accordance with the invention, the neck 18 of the anchor 10 may be angled in order to offset by a predetermined angle the first end 14a of the anchor 10 with respect to the second end 14b. In the illustrated embodiment, the barbs 24 in the two sets 14a, 14b or distributed along the two ends 14a, 14b are angled with respect to one another. Each defines a central axis, which for each end 14a, 14b will be offset from the other end's axis by some angle, typically five, ten, or fifteen degrees (usually ten or fifteen).

The illustrated embodiment shows the two ends 14a, 14b or the sets 14a, 14b of the barbs 24 being oriented to extend radially in the same directions. Thus, one may think of the two sets 14a, 14b of barbs 24 being coplanar, or to have an axis of symmetry. The plane of a flat on the side of each barb would be coplanar in each set 14a, 14b. Meanwhile, the barbs 24 at each end 14a, 14b are both required to be inserted axially into respective joints.

A function of an anchor 10 in accordance with certain embodiments is to provide a change in the relative angle between the resected joints in an operation. Thus, a surgeon may resect a face or head of a joint as appropriate at a specific angle in order to ensure that, for example, the intermediate joint 74 may be angled downward with respect to a proximal joint 70. In this way, the sets 14a, 14b of barbs 24 can each extend axially in alignment with their respective joints 70, 74 while yet maintaining the resected faces 68, 72 in compression, with the anchor 10 being in tension to maintain the force therebetween.

Figure 18:
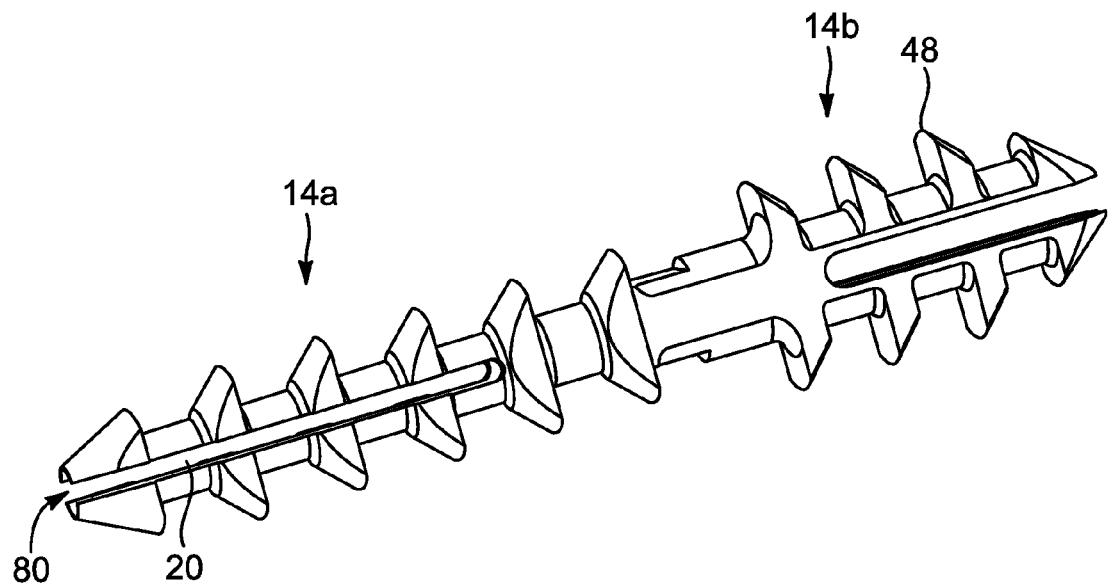
FIG. 18 is a perspective view of one embodiment of a cannulated anchor having a monolithic and homogeneous material and having barbs on both ends, in this embodiment all barbs are radially extending in the same direction.
Figure 19A:
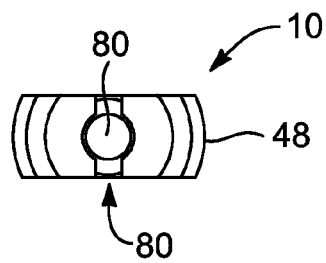
FIG. 19A is an end view of the anchor of FIG. 18.

Referring to FIGS. 18-19A, an alternative embodiment of an anchor 10 in accordance with the invention may be completely straight. In the illustrated embodiment, the barbs 24 have edges 48 oriented in the same direction. In this embodiment illustrated, the anchor 10 is provided with a cannula 80. In this embodiment, the neck 18 is also illustrated with a slot suitable for receiving the slot 58 of the tip 55 or the receiving end 55 of the buttress tool 50.

Figure 19B:
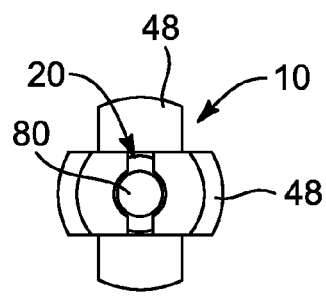
FIG. 19B is an end view of the anchor of FIG. 20.
Figure 20:
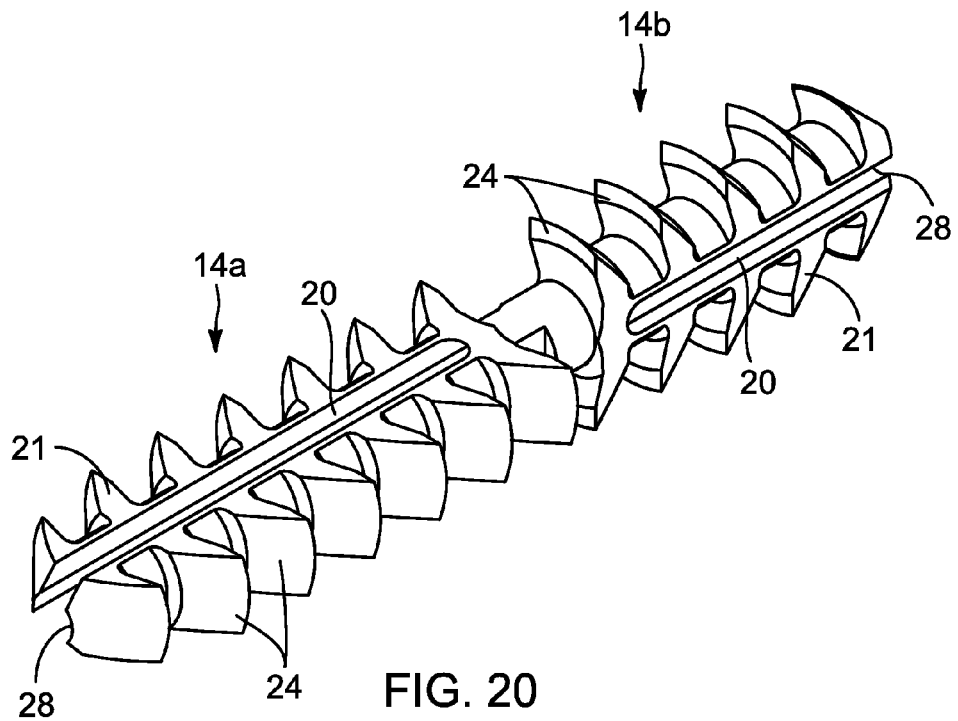
FIG. 20 is a perspective view of an alternative embodiment of one embodiment of a double-barbed anchor, homogeneously formed of a single material and having the barb sets at opposite ends thereof extending radially at directions that are circumferentially orthogonal to one another, these being 90 degrees out of phase.

Referring to FIGS. 19B-20, an alternative embodiment of an anchor may also be cannulated, and yet have the barbs extending in different directions from one another. In this embodiment, the barbs 24 of a first end 14a are rotated circumferentially (about a central axis) by 90 degrees with respect to the barbs 24 on the opposite end 14b. Inasmuch as this embodiment of an anchor 10 is straight, a cannula 80 may be formed and used profitably. Thus, each of the embodiments of FIGS. 10-20 may receive a K-wire 67 as a guide in the cannula 80 thereof.

In the embodiment of FIGS. 18-19A, and embodiments in which barbs 24 are all aligned the same at both ends 14a, 14b, the barbs 24 are all extending in the same direction and thus bear on the same cortical aspect of their respective joints 70, 74. In contrast, in the embodiment of FIGS. 19B-20, the barbs 24 at opposite ends 14a, 14b will engage aspects rotated 90 degrees with respect to one another. For example, one set of barbs will engage a side portion of a joint 70, 74 while the opposite end will engage the top and bottom portions of a cortical portion of a join 70, 74.

Figure 21:
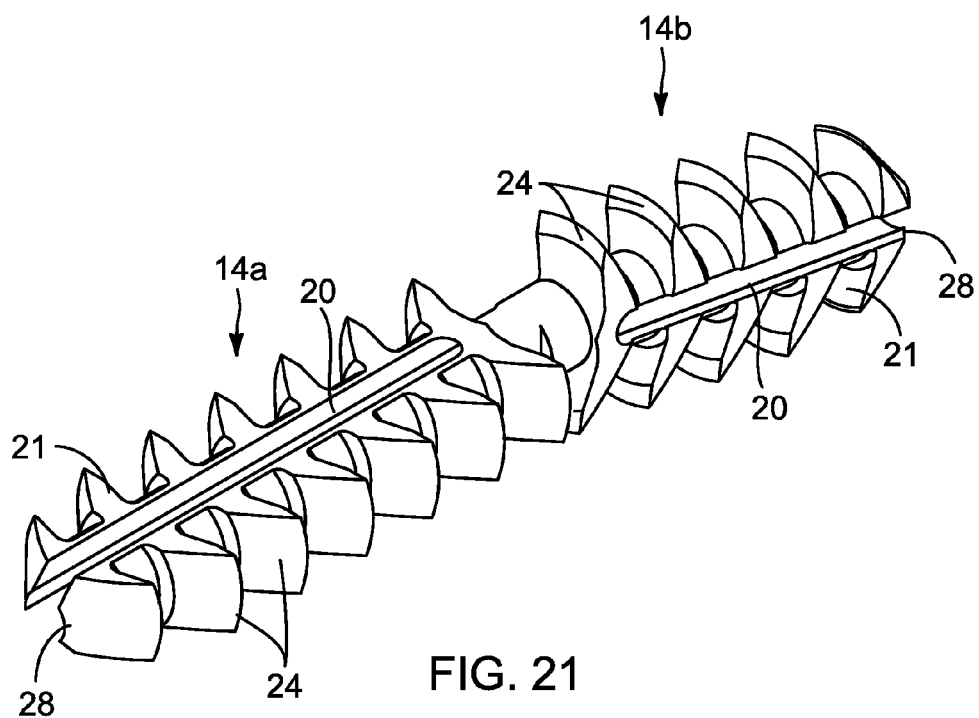
FIG. 21 is a perspective view of an alternative embodiment of the apparatus of FIG. 20, this having a bent neck between the two ends, and thus angling the axes central to the sets of barbs on either end at an angle of a suitable amount for effecting an angular displacement of one joint with respect to another for joinder.
Figure 22:
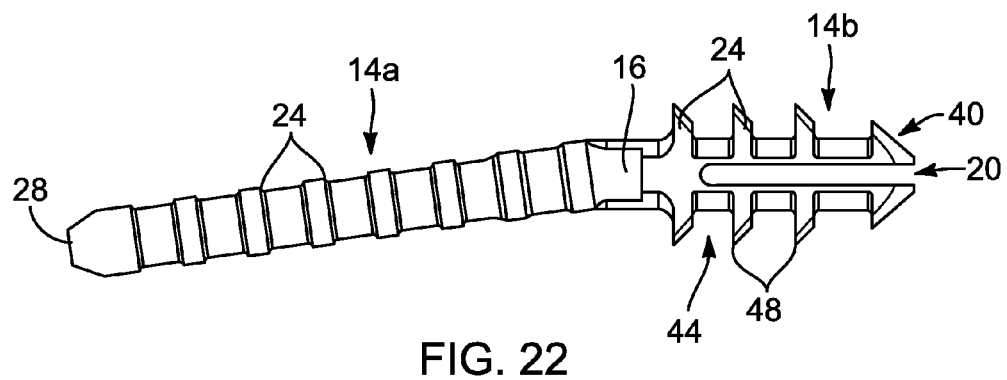
FIG. 22 is a side elevation view of the apparatus of FIG. 21.
Figure 23:
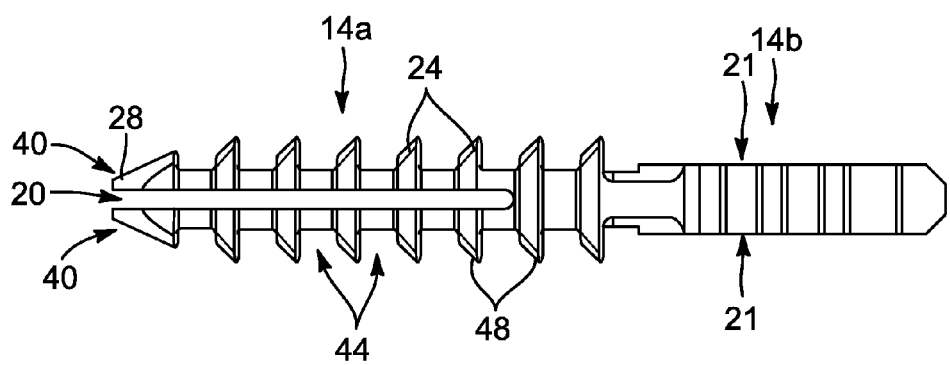
FIG. 23 is a top plan view thereof.

Referring to FIGS. 21-23, an alternative embodiment of an anchor 10 in accordance with the invention includes a bend in the neck 18, thus offsetting the central axes of sets 14a, 14b of barbs 24 or opposite ends 14a, 14b from one another at a preselected angle. Such an embodiment does not receive a K-wire 67 as such a rod 67. A K-wire 67 could not slide through a cannula 80. Accordingly, no cannula is provided in this embodiment.

Insertion of the anchor 10 of FIGS. 21-23 is nevertheless accomplished in the same manner as that of straight configurations. The angle between the opposing ends 14a, 14b is accommodated by the web 60 in the tool 11. That is, the web 60 is angled within its slot 58, thus receiving the anchor 10 therein and the slot 20 in the anchor 10 is accommodated with the angled web 60. Thus, insertion is always in a respective axial direction for the anchor 10 and the tool 11. The tool 11 still drives the first inserted end, whether the end 14a or 14b at a collinear and straight angle with respect to the axial direction of the tool 11.

Figure 24:
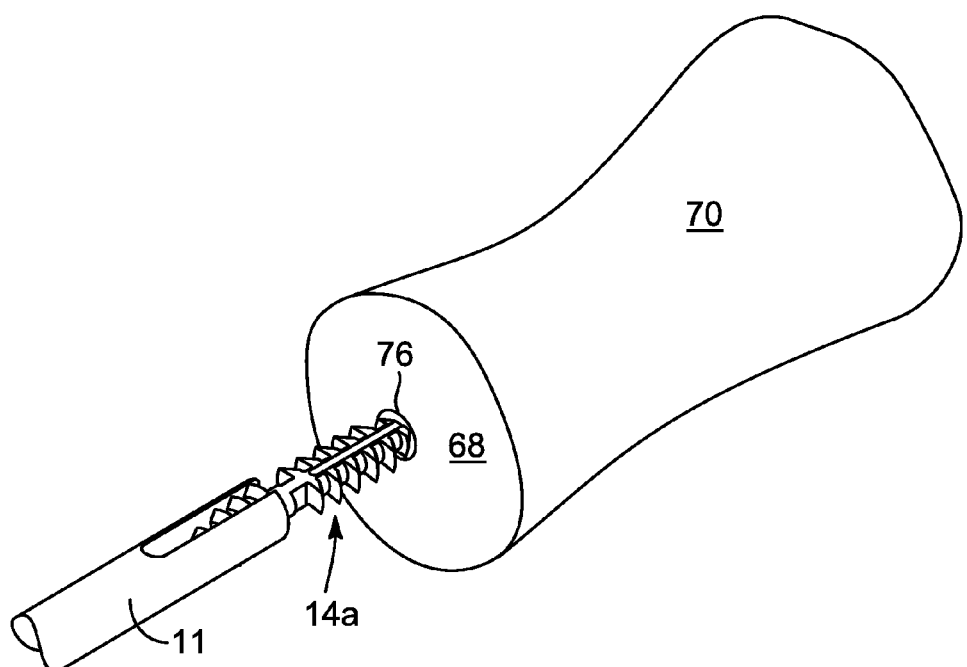
FIG. 24 is a perspective view of an anchor in accordance with the invention showing the process of engagement of a proximal end with a first bone joint.
Figure 25:
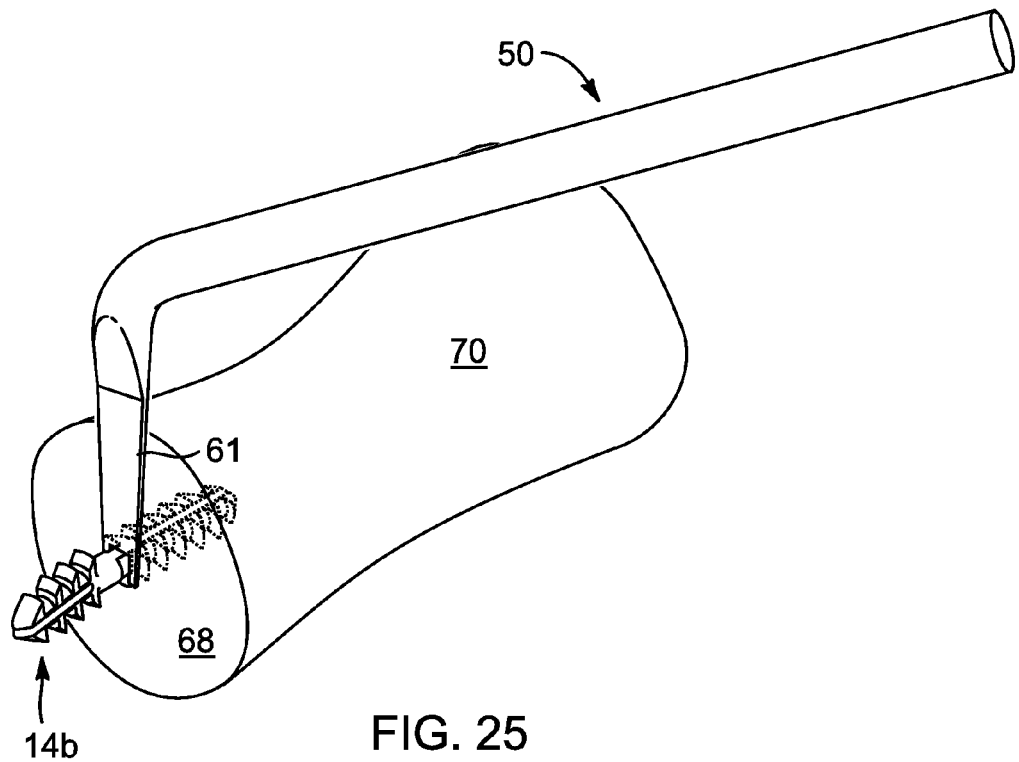
FIG. 25 is a perspective view of the anchor of FIG. 24 showing the buttressing tool in place to resist any further retreat into the first joint.
Figure 26:
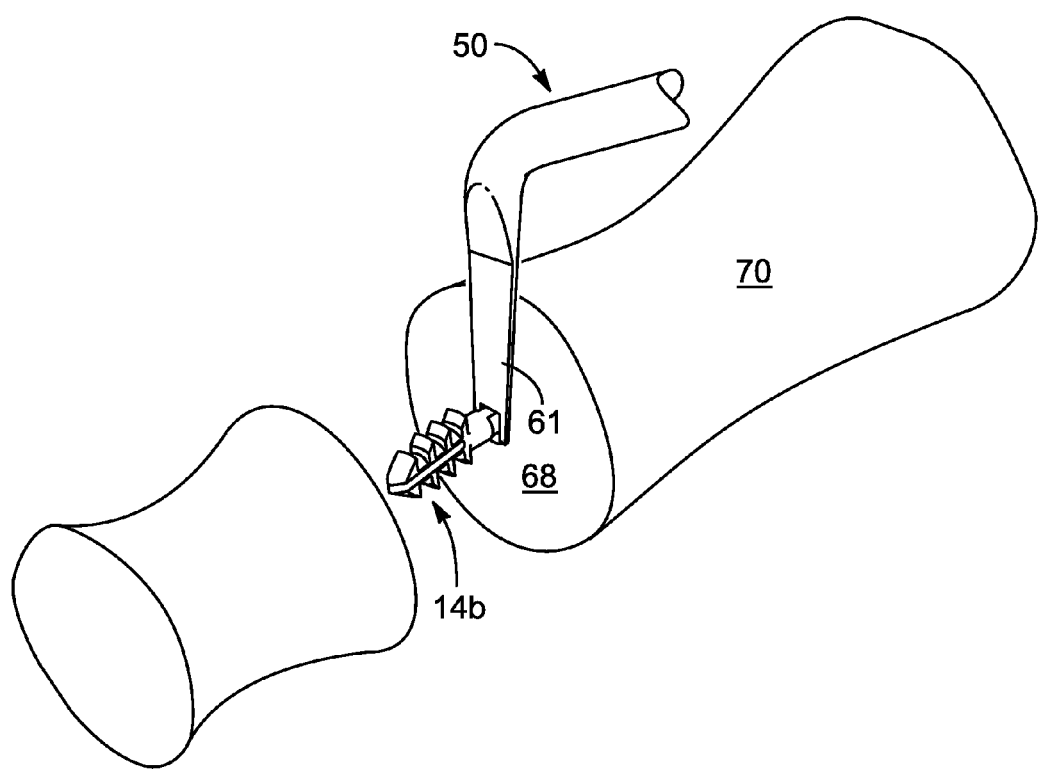
FIG. 26 is a perspective view of the anchor of FIGS. 24 and 25, as the distal barbed end thereof is inserted into the second bone joint (that is to be fused with the first bone joint) while the buttressing tool stabilizes the anchor in the first joint.
Figure 27:
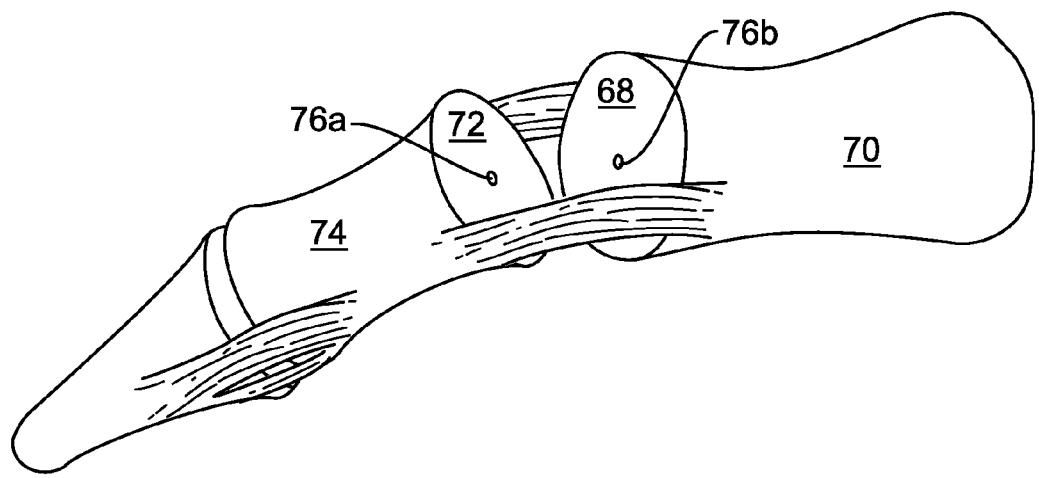
FIG. 27 is a perspective view of a joint prepared for joinder being resected and having a pilot drilled in the face thereof.

Referring to FIGS. 24-26, the use of an anchor 10 and the tools 11, 50 in a surgical operation may include several distinct steps. Some may be done simultaneously, and some may be executed sequentially.

As a preparatory matter, the face 68 of a first bone joint 70 may be trimmed, or resected in order to render the face 68 of the joint 70 capable of joining with a face 72 of another joint 74 of bone. That is, so long as the outermost layer of the joint 70 remains intact, it will not tend to heal with another bone. However, by resecting the face 68 slightly toward the bone joint 70 (proximal phalangeal joint 70), the face 68 will then be in a condition to heal against another joint 74 (intermediate phalangeal joint 74) of bone. A face 72 of the second bone joint 74 is likewise resected in order to trim it and prepare it to heal against the first joint 70.

Initially, the bone-joints 70, 74 may be drilled with pilot holes 76 (eg., 76a, 76b). An awl or drill may be used. The pilot holes 76 may be broached to a proper size and shape to receive the anchor 10. Then, the anchor 10 is placed in the tool 11.

Embodiments of an anchor 10 wherein both ends are barbed portions 14a, 14b require linear insertion of the anchor 10 with the tool 11, rather than rotation as required by threading. By a longitudinal push of the first set 14a of barbs 24 into the pilot hole 76, preferably after broaching, force is applied through the tool 11.

The tool 11 is used to drive the proximal portion 14a, and particularly the point 26 thereof is urged into the first bone joint 70.

The neck 18 in double-end-barb configurations is best formed with a slot portion 16 as a shank 16. Slots 16 are recessed into the diameter of the neck 18. The slot 16 is to be engaged by the receiving end 55 of the buttress tool 50.

Accordingly, the barbs 24 engage the medullar portion of the first bone joint 70, until the shank portion 16 of the neck 18 is effectively buried flush with the surface 68 or face 68 of the joint 70. The tool 11 may then be removed. The tool 11 has engaged one barb portion 14a, 14b of the anchor 10, thus using the other barb portion 14b, 14a as an engagement region for the joint 70. In the illustrated arrangement, the portion 14b acts as a head for the engagement by the tool 11 of the anchor 10, the other portion 14a being inserted first into a joint.

Upon withdrawal of the tool 11 along a longitudinal axis of the barb portion 14b, the tool 11 may be removed. Likewise, as the barb portion 14a drives through the face 68 of the joint 70, the face 68 eventually contacts the tool 11. Disengaging the tool 11 from the shank 16 of the anchor 10, a surgeon may now place the buttress tool 50 at the neck 18 of the anchor 10.

The slot 59 of the buttressing tool 50 engages the shank 16 or slots 16 in the neck 18. The tool 50 is gripped by its handle 53, which is offset from the receiving end 55 by a corner 57 or angle 57. Thus, a surgeon relies on the face 61 of the receiving end 55 to buttress the anchor against further insertion of the first inserted portion 14*a* into the joint 70 while the second inserted portion 14*b* is being inserted into the other joint 74.

Thereafter, the second set 14*b* of barbs 24 may be inserted into the pilot hole 76*a* of the joint 74 by pushing it into the pilot hole 76*a*. The pilots 76*a*, 76*b* are preferably broached to a size and shape suitable for receiving the respective ends 14*b*, 14*a* of the anchor 10, as described hereinabove. Thus, the joint 74 is forced onto the second set 14*b* of barbs 24, whereas the first set 14*a* of barbs 24 is forced into the face 68 of the proximal joint 70, in this embodiment of a method of application.

Rotational adjustment between the joints 70, 74 is more difficult and damaging. It should therefore be accomplished by orienting the pilots 76, consequent broached canal 78, or both. This should be done before inserting either of the barb sets 14*a*, 14*b* (ends 14*a*, 14*b*). This should be considered particularly so with the second-inserted set 14*b* of barbs 24.

Once the tool 11 has been withdrawn, the barb portion 14*b* is exposed and projecting from the joint 70, and particularly from the face 68 thereof. A pilot hole 76*a*, previously or now drilled into the face 72 of the joint 74 provides a certain amount of relief, and directional piloting of the barb portion 14*b*. with the buttressing tool 11 in place to stop further receding of the anchor 10, the surgeon may then push the point 28 of the remaining barb portion 14*b* into the pilot hole 76*a*.

Thus the barb portion 14*a* is initially guided and engaged in the pilot hole 76*b* or channel 78 in the first joint 70. At this next stage, the barb portion 14*b* is driven by force into the pilot 76*a* or broached channel 78 in the second joint 74.

The cantilevered prongs 40 will move toward one another, thus providing relief on the edges 48 of the barbs 24. However, upon any tendency to come to rest, or to be withdrawn, each of the edges 48 immediately cuts and drives outward due to the undercut shaping thereof. Thus, the barbs 24 provide a positive force, in tension, holding the face 72 of the second joint 74 against the face 68 of the first joint 70 in compression.

At this point, the faces 68, 72 are typically in full planar contact. Inasmuch as each of the faces 68, 72 is resected, typically by a saw or other tool capable of forming a planar surface 68, 72. Alignment of the faces 68, 72 is achieved, as needed for best healing. Nevertheless, in order to obtain that alignment, a surgeon may have resected at a pre-selected angle and use the correspondingly angled anchor 10 (e.g., FIGS. 10-15, 21) to maintain that alignment.

After reduction, stability against relative rotation between the joints 70, 74 during healing is provided by the flats 21 of the two barbed portions 14*a*, 14*b*. Stability and tensioning in a longitudinal direction (and thus compression to urge union) is provided by the barbs 24.

Final adjustments in a longitudinal direction may be made by the reduction advancing the joints together with the buttress tool 50 removed. This further advances at least one and possibly both of the ends 14*a*, 14*b* of barbs 24. Rotational adjustments may be made by rotating the joint, but will be resisted by the barb portions 14*a*, 14*b* since there is no screw portion 12 in this embodiment. Angular adjustments are not made by bending the anchor in this embodiment. The anchor defines the angle, whether zero degrees, ten degrees, or fifteen degrees, as required by the shape of the intermediate joint 74.

Referring to FIGS. 27-31, an alternative embodiment of a method in accordance with the invention, and using the apparatus 10 in accordance with the invention, a cannulated anchor 10 may be used with a K-wire 67 to remain after completion of the surgery and removed only after a substantial portion of healing.

For example, a joint 70 which would otherwise be first to receive the insertion of an anchor 10 may actually be left until last. Upon opening of the joints 70, 74, as known in the art, by a preparation and draping of the foot, a dorsal incision made along a dorsal proximal interphalangeal joint will expose the joints 70, 74.

Once the skin is incised, a tenotony is made. It is important to create a good distal tenotomy flap for subsequent closure. Typically, an inversion technique closure will be performed on the joints 70, 74. Thus, an adequate distal flap is required. Medial and lateral ligaments to the head of the proximal joint are transected.

The head of the proximal phalanx is then removed with a sagittal saw or sagittal bone cutting tool. The cut made may be either perpendicular to the long axis of the intermediate phalanx or may be angled. Typically, the resection of the proximal phalanx will typically always be perpendicular to the longitudinal axis thereof.

The articular cartilage on the base of the intermediate phalanx 70 is then removed. Any rough areas of bone may be removed with a rougher, operating much as a file or rasp. The toe must then be checked for proper reduction and alignment. It may be required to sequentially release to plantarflex the remaining proximal phalanx.

An awl, drill, or both may be used to create a pilot 76 for receiving a broach 66 of a broaching tool 65. The smallest distal broach will typically be used and typically with the dorsal side up on the intermediate phalanx 74. Typically, it is recommended that three sizes of broach be used. They should lead up to the best size to fit the canal 78 or broached opening 78 that will eventually receive the anchor 10.

Once the proper size has been determined, then the proximal phalanx 70 may be piloted, leaving a pilot 76*b* therein. Again, proximal broaches may broach up to the same size.

Figure 28:
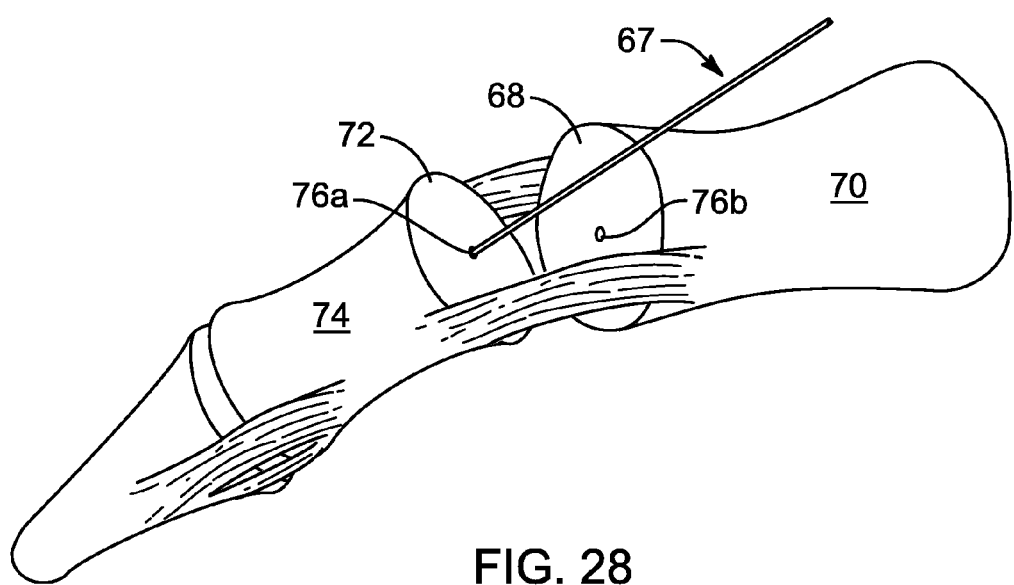
FIG. 28 is a perspective view of the set of joints of FIG. 27, this being subject to an alternative embodiment of a method for joinder, and relying on a K-wire inserted in the pilot in the face of the intermediate joint to act as a guide and as a structural member.
Figure 29:
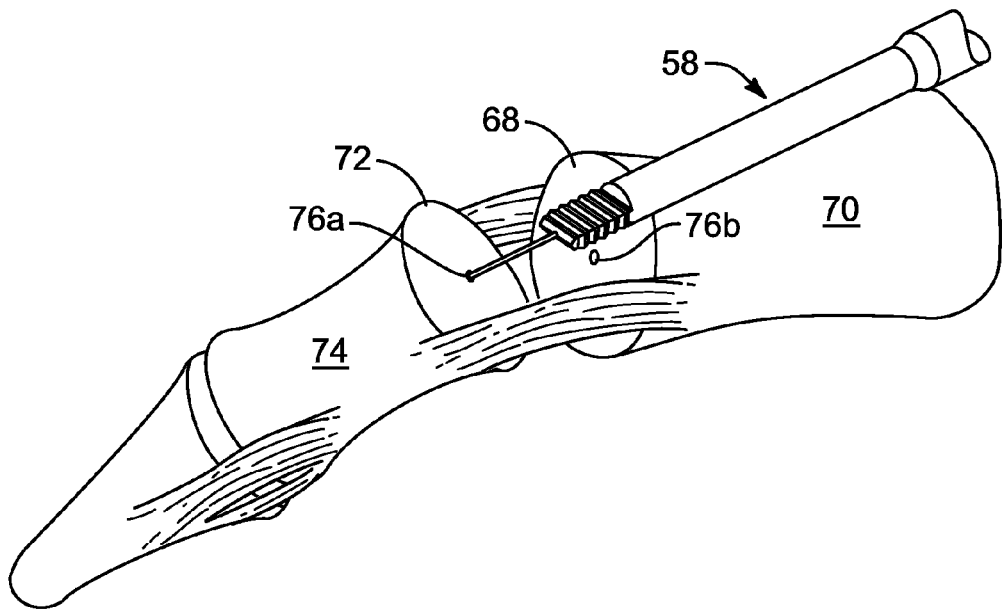
FIG. 29 is a perspective view of the joints of FIGS. 27-28, having the K-wire in place, and a broaching tool guided by the K-wire to form a larger and more properly shaped opening for receiving an apparatus in accordance with the invention.

Referring to FIG. 28, and with reference to FIGS. 28-31, a K-wire 67 may be inserted into the intermediate phalangeal joint 74, through the pilot 76*a*. In the illustrated embodiment, the K-wire is used as a guide to receive the broaching tool 65. As illustrated in FIG. 29, the broach 65 or broaching tool 65 may thus ride the K-wire 67, in order to maintain the direction and dimensional integrity of the opening 74 to be formed by the broach 65.

For example, the k-wire 67 may actually penetrate the joint 74 and may eventually penetrate the joint distal thereto.

In the illustrated embodiment, the cannula 69 of the broaching tool 65 rides along the outside of the K-wire 67. Thus, each stroke with the broach 65 is always along exactly the same axis. Likewise, as multiple broaches 65 are used to begin at a size close to that of the pilot 76*a*, and increase up to the size of the anchor 10 to be inserted therein, the axis is always defined by the K-wire 67 and maintained.

Figure 30:
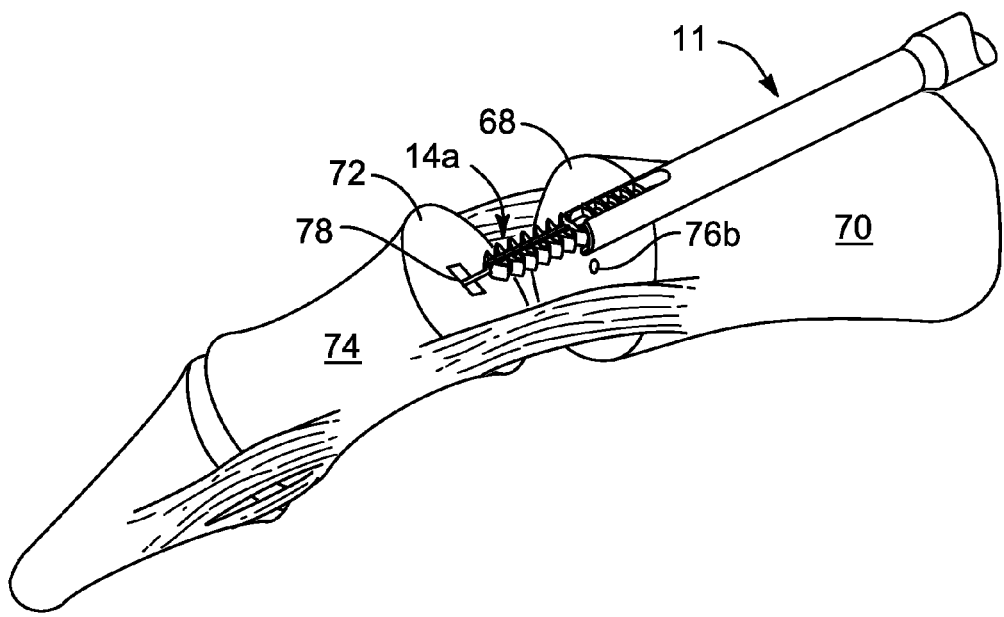
FIG. 30 is a perspective view of FIGS. 27-29, illustrating a tool prepared to insert an anchor therein into the intermediate joint in accordance with one embodiment of a method and apparatus in accordance with the invention.
Figure 31:
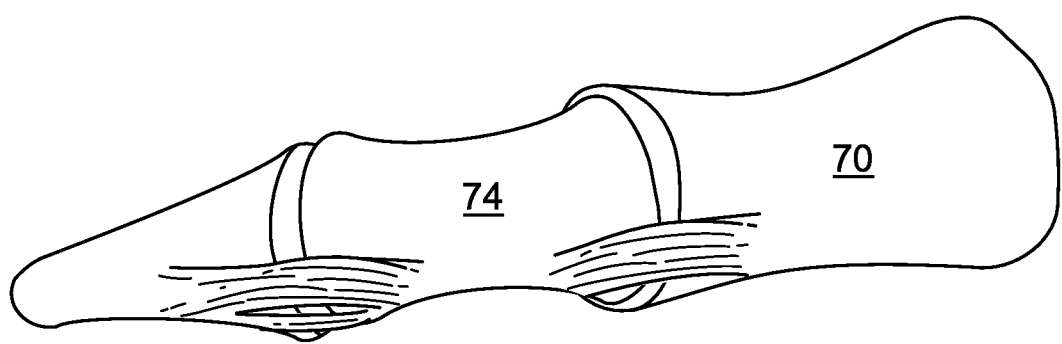
FIG. 31 is a perspective view of the joints of FIGS. 27-30, having the joints formed together and the K-wire guide extending out therefrom, for maintaining stability until a suitable time during the healing process, when the K-wire can be removed.

Referring to FIG. 30, once the opening 78 has been broached to the proper size to receive the first end 14*a* of the anchor 10, the insertion too 11 may receive the implant 10 or anchor 10 in the slot 58 therein. In this embodiment of a method, the tool 11 may drive the first end 14a of the anchor 10 into the canal 78 the full distance required. Thereupon the buttress tool 50 may be placed at the neck 18 of the anchor 10 in order to preclude any further penetration of the end 14a into the joint 74. At this point, the tool 11 may be removed and the K-wire 67 may be driven to a distance within the length of the anchor 10. Accordingly, the surgeon may then grasp the joint 74 and the buttress tool 50 and force the second end 14b of the anchor into the pilot 76b which has also been broached by the broaching tool 65. In this way, the faces 68, 72 will be placed in contact with the anchor 10 maintaining tension within itself and thus compression between the faces 68, 72.

As can be appreciated, the method of the illustrated embodiment of FIGS. 27-31 may only be used with a straight anchor 10. A K-wire 67 cannot effectively guide or slide along a cannula 80 of an anchor 10 that has a bend or an angle at the neck 18.

Once a first canal 78 has been sized an broached, the opposing canal in the other remaining joint 70, 74 must be considered. For example, depending on whether the barbs 24 are rotated between the two ends 14a, 14b, whether the anchor 10 is cannulated, and whether the anchor has any bend all, one must consider the angle at which the pilot 76 and subsequent broached opening 78 will proceed.

Typically, when one is operating without a K-wire as a guide 67, the proximal side of the anchor 10 is inserted first, or the proximal joint 70 receives the anchor 10 first. Then the buttress instrument 50 is used to stabilize the implant and maintain its axial position within the first joint.

Otherwise, the intermediate phalangeal joint 74 is first penetrated by the anchor 10 after which the K-wire 67 is driven out through the end of the toe but remains within the cannula 80 of the anchor 10. It remains while the reduction is made. It is shortened, by displacement out the intermediate joint 74. Then, by driving the intermediate phalangeal joint 74 with the anchor 10 secured therein and stabilized by the buttressing tool 50, a surgeon inserts the remaining end 14b of the anchor 10 into the broached opening 78 of the remaining proximal joint 70.

The joints 70, 74 are reduced, with the anchor 10 providing tension. This draws the joints 70, 74 together, each in compression against the other. A standard closure may be applied to the operation area. Suitable dressings and protection may then be provided to protect the K-wire 67 from being dislocated or causing disruption. Thereafter, the K-wire 67 may be removed at the proper stage of healing.

The present invention may be embodied in other specific forms without departing from its principles of operation essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of arthrodesis, the method comprising:
    providing an anchor, comprising a monolithic, homogeneously formed structure, comprising
        a first end comprising a first prong and a second prong extending longitudinally along a first longitudinal axis, the first prong containing first barbs facing outward in a first radial direction, the second prong containing second barbs facing outward in a second radial direction opposite the first radial direction such that a first plane bisects the first prong and the second prong and the first barbs and the second barbs along the first longitudinal axis, the first prong and the second prong separated by a first open slot, the first open slot having a first mid-plane equally spaced between the first prong and the second prong, the first mid-plane orthogonal to the first plane;
        a second end comprising a third prong and a fourth prong extending longitudinally along a second longitudinal axis, the third prong provided with third barbs extending outward therefrom in a third radial direction, the fourth prong containing fourth barbs extending in a fourth radial direction opposite the third radial direction, such that a second plane bisects the third prong and the fourth prong and the third barbs and the fourth barbs along the second longitudinal axis, the third prong and the fourth prong separated by a second open slot, the second open slot having a second mid-plane equally spaced between the third prong and the fourth prong, the second mid-plane orthogonal to the second plane, the second mid-plane rotated 90 degrees about the second longitudinal axis with respect to the first mid-plane, and
        a neck, extending longitudinally between the first and second ends, the neck having an engagement region;
    accessing a head of a proximal phalangeal joint of a subject;
    accessing a base of an intermediate phalangeal joint of the subject;
    forming a first interface surface by resecting the head;
    forming a second interface surface by resecting the base;
    drilling a first pilot in the head through the first interface surface;
    drilling a second pilot in the base through the second interface surface;
    inserting the first end into one of the first and second pilots;
    fitting a buttressing tool to the engagement region, the buttressing tool having a handle portion, an anchor receiving portion, and a corner joining the handle portion and the anchor receiving portion such that the anchor receiving portion is disposed at an oblique angle with respect to the handle portion, wherein the anchor receiving portion of the buttressing tool has a thickness, the thickness being less than a pitch between adjacent first barbs along the first prong; and
    placing the first and second interface surfaces in contact by urging the second end into the other of the first and second pilots, wherein the buttressing tool resists insertion of the first end farther into the one of the first and second pilots during the urging of the second end into the other of the first and second pilots.

2. The method of claim 1, wherein:
    the first and second prongs are cantilevered between a base region thereof proximate the neck and a separation region spaced therefrom; and
    the third and fourth prongs are cantilevered proximate the neck and extend away therefrom.

3. The method of claim 1, wherein the proximal and intermediate joints each comprise a cortical portion, formed of a comparatively harder and stronger material proximate an outer boundary thereof, and a medullar portion, formed of a comparatively softer and weaker material proximate a central axis thereof, the method further comprising:
    urging at least one of the first, second, third, and fourth prongs toward the corresponding longitudinal axis due to compression of the corresponding first, second, third or fourth barbs by pressure from at least the corresponding medullar portion acting thereon; and urging of edges of the corresponding first, second, third or fourth barbs, by cantilevered loads from the corresponding first, second, third, or fourth prongs, to engage the corresponding cortical portion.

4. The method of claim 1, further comprising:
orienting the first and second interface surfaces with respect to one;
removing the buttressing tool; and
urging the first and second interface surfaces together.

5. The method of claim 4, further comprising:
compressing of the prongs toward the corresponding longitudinal axis in response to movement of the barbs with respect to the medullar region; and
urging of the barbs away from the corresponding longitudinal axis by residual bending forces remaining in the prongs from displacement in response to the compressing.

6. The method of claim 5, further comprising engaging of a cortical portion of the corresponding joint by edges of the barbs in response to the urging of the barbs away from the corresponding longitudinal axis.

7. A method comprising:
providing an anchor, comprising
a first portion comprising a first prong and a second prong extending longitudinally along a first longitudinal axis, the first prong containing first barbs extending in a first radial direction, the second prong containing second barbs extending in a second radial direction opposite the first radial direction, such that a first plane bisects the first prong and the second prong and the first barbs and the second barbs along the first longitudinal axis, the first prong and the second prong separated by a first open slot, the first open slot having a first mid-plane equally spaced between the first prong and the second prong, the first mid-plane orthogonal to the first plane;
a second portion comprising a third prong and a fourth prong extending longitudinally along a second longitudinal axis, the third prong provided with third barbs extending in a third radial direction, the fourth prong containing fourth barbs extending in a fourth radial direction opposite the third radial direction such that a second plane bisects the third prong and the fourth prong and the third barbs and the fourth barbs along the second longitudinal axis and wherein the third prong and the fourth prong are separated by a second open slot, the second open slot having a second mid-plane equally spaced between the third prong and the fourth prong, the second mid-plane orthogonal to the second plane, the second mid-plane rotated 90 degrees about the second longitudinal axis with respect to the first mid-plane,
a neck disposed between and interconnecting the first and second portions;
the first and second portions and neck being formed as a monolithic, homogeneously formed unit;
providing a tool having a receiving portion shaped to receive at least one of the first and second portions, the tool having a web configured to be inserted in at least one of the first open slot and the second open slot;
accessing a head of a first joint of a subject;
accessing a base of an adjacent joint of the subject;
placing the anchor in the tool;
applying force to the anchor through the tool;
penetrating the first portion into one of the head and the base by the applying force;
removing the tool to leave the anchor emplaced;
penetrating the second portion into the other of the head and the base by urging the base toward the head in a linear translation; and
placing the head and the base into mutual contact by the urging.

8. The method of claim 7, further comprising:
forming a first interface surface by resecting the head; and
forming a second interface surface by resecting the base.

9. The method of claim 7, wherein:
the neck is provided with an engagement portion;
the method further comprises providing a buttressing tool fitted to the engagement portion to resist longitudinal motion of the anchor; and
the buttressing tool supports the anchor against further penetration into the one of the head and the base during the penetrating the second portion into the other of the head and the base.

10. The method of claim 9, further comprising:
drilling a first pilot in the head through a first interface surface; and
drilling a second hole in the base through a second interface surface.

11. The method of claim 7, wherein
the providing further comprises providing a buttressing tool engaging the neck to resist further penetrating by the first portion during penetrating by the second portion.

12. The method of claim 7, wherein the first joint is a proximal phalangeal joint and the second joint is an intermediate phalangeal joint.

* * * * *